(12) United States Patent
Furuya et al.

(10) Patent No.: US 11,892,438 B2
(45) Date of Patent: Feb. 6, 2024

(54) OPTICAL DENSITOMETER AND OPTICAL WAVEGUIDE

(71) Applicant: Asahi Kasei Microdevices Corporation, Tokyo (JP)

(72) Inventors: Takaaki Furuya, Tokyo (JP); Tatsushi Yagi, Tokyo (JP); Toshiro Sakamoto, Tokyo (JP)

(73) Assignee: Asahi Kasei Microdevices Corporation, Tokyo (JP)

( * ) Notice: Subject to any disclaimer, the term of this patent is extended or adjusted under 35 U.S.C. 154(b) by 617 days.

(21) Appl. No.: 17/115,792

(22) Filed: Dec. 9, 2020

(65) Prior Publication Data
US 2021/0181103 A1 Jun. 17, 2021

(30) Foreign Application Priority Data

Dec. 12, 2019 (JP) .................................. 2019-224818
Dec. 12, 2019 (JP) .................................. 2019-224937
Dec. 12, 2019 (JP) .................................. 2019-224941

(51) Int. Cl.
*G01N 33/00* (2006.01)
*G01N 21/552* (2014.01)
(Continued)

(52) U.S. Cl.
CPC ....... *G01N 33/0027* (2013.01); *G01N 21/552* (2013.01); *G01N 21/5907* (2013.01);
(Continued)

(58) Field of Classification Search
CPC ............ G01N 21/552; G01N 21/5907; G01N 33/0027; G01N 2201/0635;
(Continued)

(56) References Cited

U.S. PATENT DOCUMENTS

2010/0322555 A1* 12/2010 Vermeulen ............... G02B 6/34
385/28
2015/0177459 A1 6/2015 Van Campenhout et al.
2020/0116631 A1 4/2020 Sakamoto et al.

FOREIGN PATENT DOCUMENTS

JP 2005300212 A 10/2005
JP 2015118372 A 6/2015
(Continued)

Primary Examiner — Benjamin R Schmitt
(74) Attorney, Agent, or Firm — KENJA IP LAW PC

(57) ABSTRACT

Provided is an optical densitometer for measuring a density of a gas or liquid of interest, the optical densitometer comprising: a light source capable of introducing light into a core layer; a detector capable of receiving the light that has propagated through the core layer; and an optical waveguide, the optical waveguide comprising: a substrate; and the core layer comprising a light propagation portion capable of propagating the light in an extending direction of the light propagation portion, and a diffraction grating portion, the diffraction grating portion comprising a diffraction grating region and an extension region connected to the diffraction grating region, and a first optical coupling region included in the extension region and a second optical coupling region included in the light propagation portion being optically coupled with respect to the light propagating through the core layer.

18 Claims, 11 Drawing Sheets

(51) Int. Cl.
    *G02B 6/42*    (2006.01)
    *G01N 21/59*   (2006.01)
    *G02B 6/122*   (2006.01)
    *G02B 6/12*    (2006.01)
    *G02B 6/124*   (2006.01)
(52) U.S. Cl.
    CPC ......... *G02B 6/122* (2013.01); *G02B 6/12002*
        (2013.01); *G02B 6/124* (2013.01); *G02B*
        *6/4215* (2013.01); *G01N 2201/0635* (2013.01);
                                  *G01N 2201/08* (2013.01)
(58) Field of Classification Search
    CPC ............ G01N 2201/08; G02B 6/12002; G02B
                    6/122; G02B 6/124; G02B 6/4215
    See application file for complete search history.

(56)           References Cited

FOREIGN PATENT DOCUMENTS

JP         2017003607 A     1/2017
WO         2018179752 A1   10/2018
WO     WO-2018179752 A1 *  10/2018   ......... G01N 21/3504

\* cited by examiner

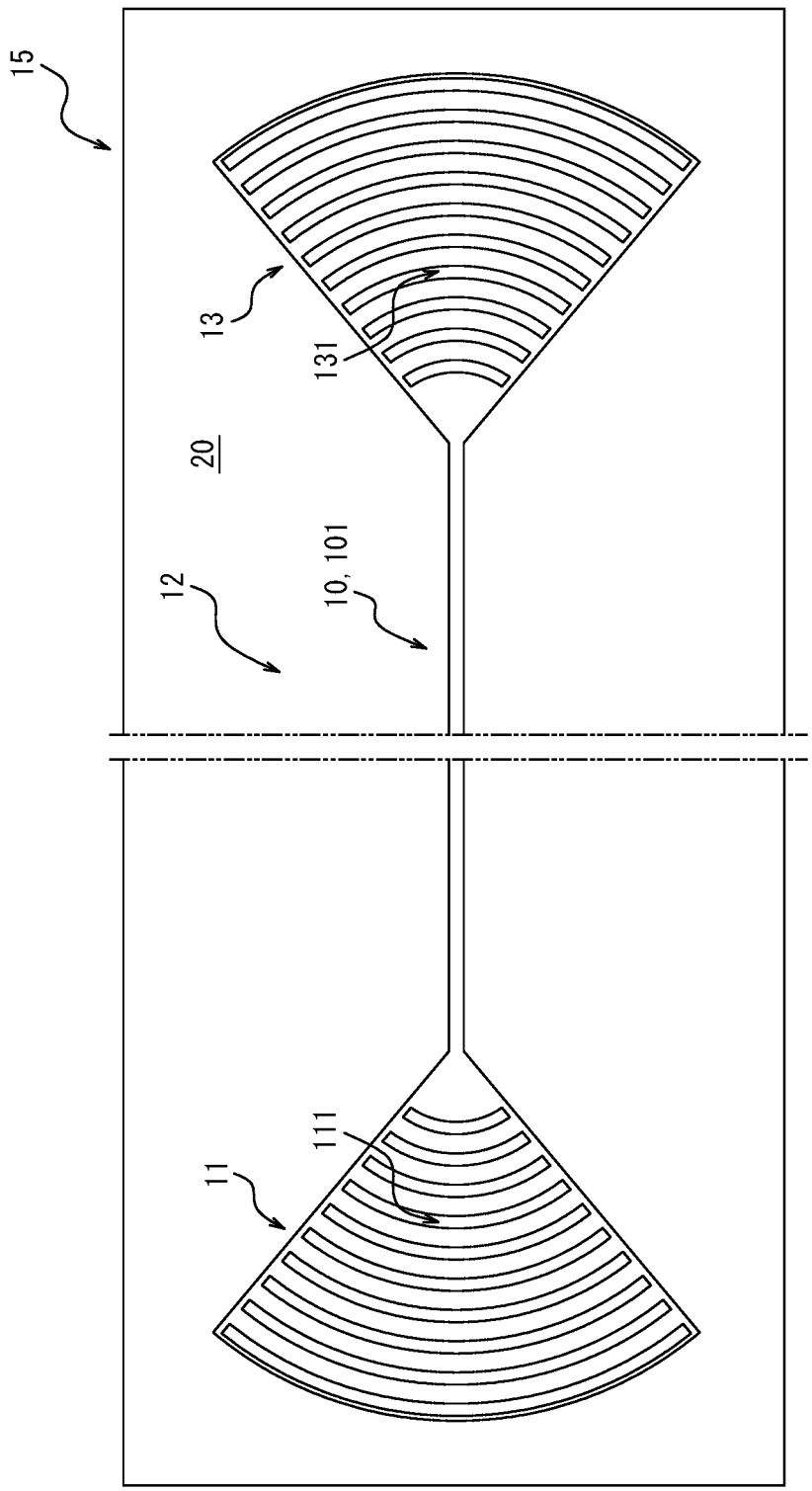

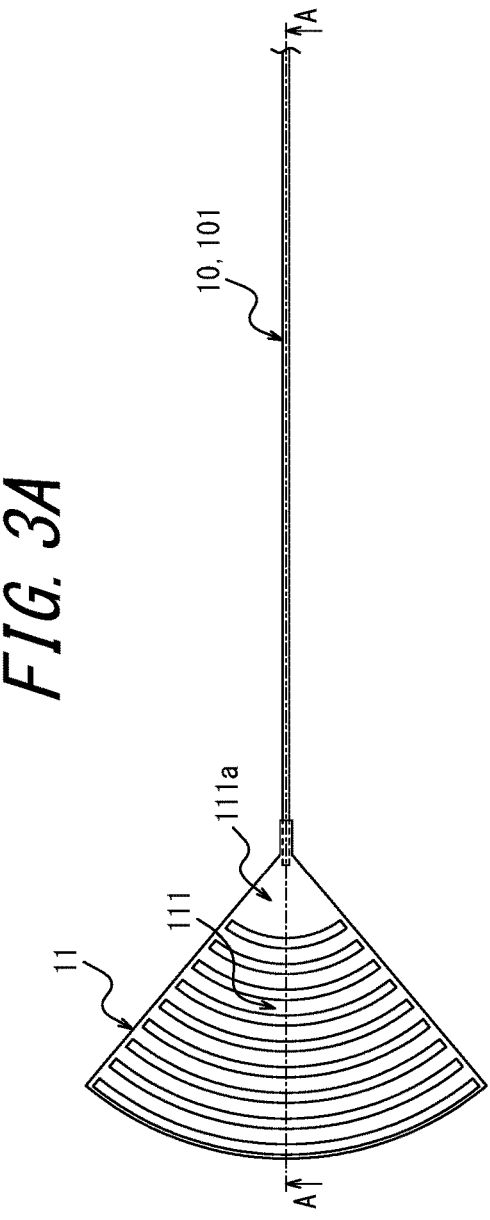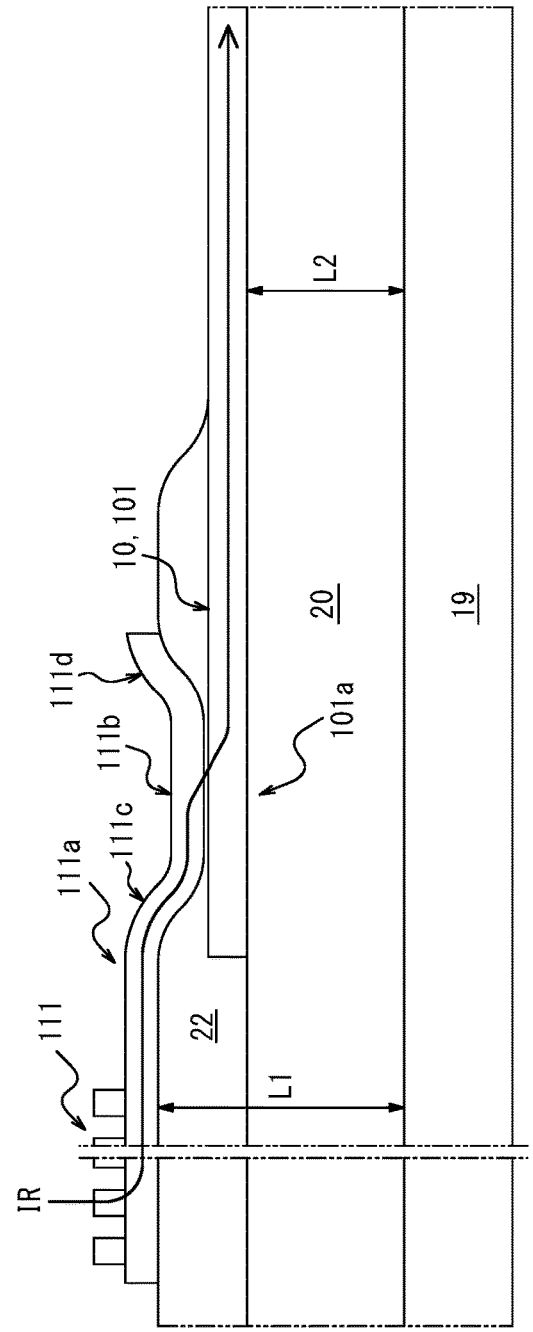

OPTICAL DENSITOMETER AND OPTICAL WAVEGUIDE

CROSS-REFERENCE TO RELATED APPLICATION

The present application claims priority to and the benefit of Japanese Patent Application No. 2019-224937 filed Dec. 12, 2019, Japanese Patent Application No. 2019-224818 filed Dec. 12, 2019, and Japanese Patent Application No. 2019-224941 filed Dec. 12, 2019, the entire contents of which are incorporated herein by reference.

TECHNICAL FIELD

The present disclosure relates to an optical densitometer and an optical waveguide.

BACKGROUND

When the refractive index of a material forming a structure, such as a thin film formed by crystals or the like, is greater than the refractive index of the material outside the structure, light propagating through the structure progresses while repeatedly undergoing total reflection at the boundary between the structure and the outside of the structure. When the light propagating through the structure is totally reflected at the boundary, the light extends to the outside, which has a smaller refractive index. Such an extension is referred to as an evanescent wave (see FIG. 14). An evanescent wave EW may be absorbed by a substance 52 adjacent to the structure 51 while light L is propagating. This enables detection and identification of the substance 52 in contact with the structure 51 based on a change in the intensity of the light L propagating through the structure 51. An analytical technique employing the above-described principle of evanescent waves EW is referred to as an attenuated total reflection (ATR) technique and is used to analyze the chemical composition of the substance 52, for example. Typically, infrared radiation is used as the light to be propagated. Substances have the property of selectively absorbing infrared radiation of particular wavelengths. A substance of interest can therefore be analyzed or sensed by causing infrared radiation corresponding to the absorption spectrum of the substance to be propagated.

Patent literature (PTL) 1 proposes an optical waveguide sensor in which the ATR technique is applied to a sensor. This optical waveguide sensor has a core layer formed on a substrate, allows light to pass through the core layer, and uses an evanescent wave to detect a substance in contact with the core layer.

CITATION LIST

Patent Literature

PTL 1: JP2005-300212A

SUMMARY

A sensor employing the ATR technique requires a location for introducing light from a light source into a core layer of an optical waveguide, as well as a location for extracting light from the core layer of the optical waveguide towards a photodetector. A diffraction grating portion for bending the optical axis of the light is therefore often provided as a part of the core layer in each of the location for introducing light from the light source into the core layer of the optical waveguide and the location for extracting the light from the core layer of the optical waveguide towards the photodetector. Such diffraction grating portions are required to be structured so as to suit the sizes and shapes of the light source and the photodetector in view of efficient light inputs to the optical waveguide or efficient light outputs from the optical waveguide.

Further, in a diffraction grating portion for extracting light from the core layer, as illustrated in FIG. 15A, when light propagating through the core layer is diffracted toward the external side D1, the diffracted light has light component La that is bent from a diffraction grating region 331 toward the external side D1 (the surface side in the thickness direction), as well as light component Lb that is bent toward the substrate side D2 in the thickness direction of the optical waveguide. After the light component Lb thus bent toward the substrate side D2 reaches the boundary with (surface of) the substrate 39, it may be reflected at the boundary back to the diffraction grating region 331. As a result, the light component Lb reflected back to the diffraction grating region 331 may interfere with the light component La extracted from the diffraction grating region 331 to the external side D1 without being reflected, in the diffraction grating region 331. Thus, in order to efficiently extract light from the diffraction grating region 331 to the external side D1, it is important to control the phase difference between the reflected light component Lb and the non-reflected light component La, in other words, to control the distance L1 between the diffraction grating region 331 and the substrate 39 to a certain value.

In the meantime, in such a sensor, the light introduced into the core layer needs to extend from a light propagation portion as an evanescent wave and be absorbed by the external substance of interest, as described above. It is thus preferable to increase the propagation distance of light through the light propagation portion (propagation channel), and to cause more evanescent waves to extend, for the purpose of improving the sensitivity of a sensor. In the case where the substrate of the optical waveguide, however, is in immediate proximity to the light propagation portion, an evanescent wave extending from the light propagation portion may reach the substrate, and a part of light propagating through the light propagation portion may leak to the substrate. In order to suppress leakage of evanescent waves to the substrate to thereby improve the propagation efficiency, it is thus important to control the distance between the light propagation portion and the substrate to a certain value, as in the distance between the diffraction grating region and the substrate.

In such a sensor, the diffraction grating portions and the light propagation portion are provided as the core layer. The required functions, shape, size, and material of the diffraction grating portions, however, differ from the functions required for the light propagation portion. Further, it is required to design the distance between the diffraction grating region and the substrate and the distance between the light propagation portion and the substrate by taking into consideration the diffraction efficiency of the diffraction grating region and the propagation efficiency of the light propagation portion in the optical waveguide.

In a conventional optical waveguide, however, because a light propagation portion and a diffraction grating region are formed on a flat support layer as a single core layer on a silicon-on-insulator (SOI) substrate or the like. It is thus difficult to optimize the shape, size, and material of the diffraction grating portions independently from those of the light propagation portion. In a conventional optical waveguide, it is also difficult to optimize the distance between the light propagation portion and the substrate and the distance between the diffraction grating region and the substrate independently from each other. It has thus been difficult to fabricate a sensor provided with a diffraction grating portion and a light propagation portion both exhibiting high performances.

It thus would be helpful to provide an optical densitometer and an optical waveguide provided with a diffraction grating portion and a light propagation portion both exhibiting high performances as a core layer.

To achieve the above, an aspect of the present disclosure is an optical densitometer for measuring a density of a gas or liquid of interest, the optical densitometer comprising:
  a light source capable of introducing light into a core layer;
  a detector capable of receiving the light that has propagated through the core layer; and
  an optical waveguide, the optical waveguide comprising:
    a substrate; and
    the core layer comprising a light propagation portion capable of propagating the light in an extending direction of the light propagation portion, and a diffraction grating portion,
  the diffraction grating portion comprising a diffraction grating region and an extension region connected to the diffraction grating region, and
  a first optical coupling region included in the extension region and a second optical coupling region included in the light propagation portion being optically coupled with respect to the light propagating through the core layer.

Further, to achieve the above, another aspect of the present disclosure is an optical waveguide for use in an optical densitometer for measuring a density of a gas or liquid of interest, the optical waveguide comprising:
  a substrate; and
  a core layer comprising a light propagation portion capable of propagating light in an extending direction of the light propagation portion, and a diffraction grating portion,
  the diffraction grating portion comprising a diffraction grating region and an extension region connected to the diffraction grating region, and
  a first optical coupling region included in the extension region and a second optical coupling region included in the light propagation portion being optically coupled with respect to the light propagating through the core layer.

The present disclosure can provide an optical densitometer and an optical waveguide provided with a diffraction grating portion and a light propagation portion both exhibiting high performances as a core layer.

BRIEF DESCRIPTION OF THE DRAWINGS

In the accompanying drawings:

FIG. 2 is a schematic plan view illustrating the optical waveguide in FIG. 1 from a light source side or a photodetector side;

FIG. 3A is a schematic plan view illustrating a part of a first diffraction grating portion and a propagation channel of the optical waveguide in FIG. 1;

FIG. 3B is a cross-sectional view illustrating a cross section along the line A-A;

DETAILED DESCRIPTION

Figure 1:
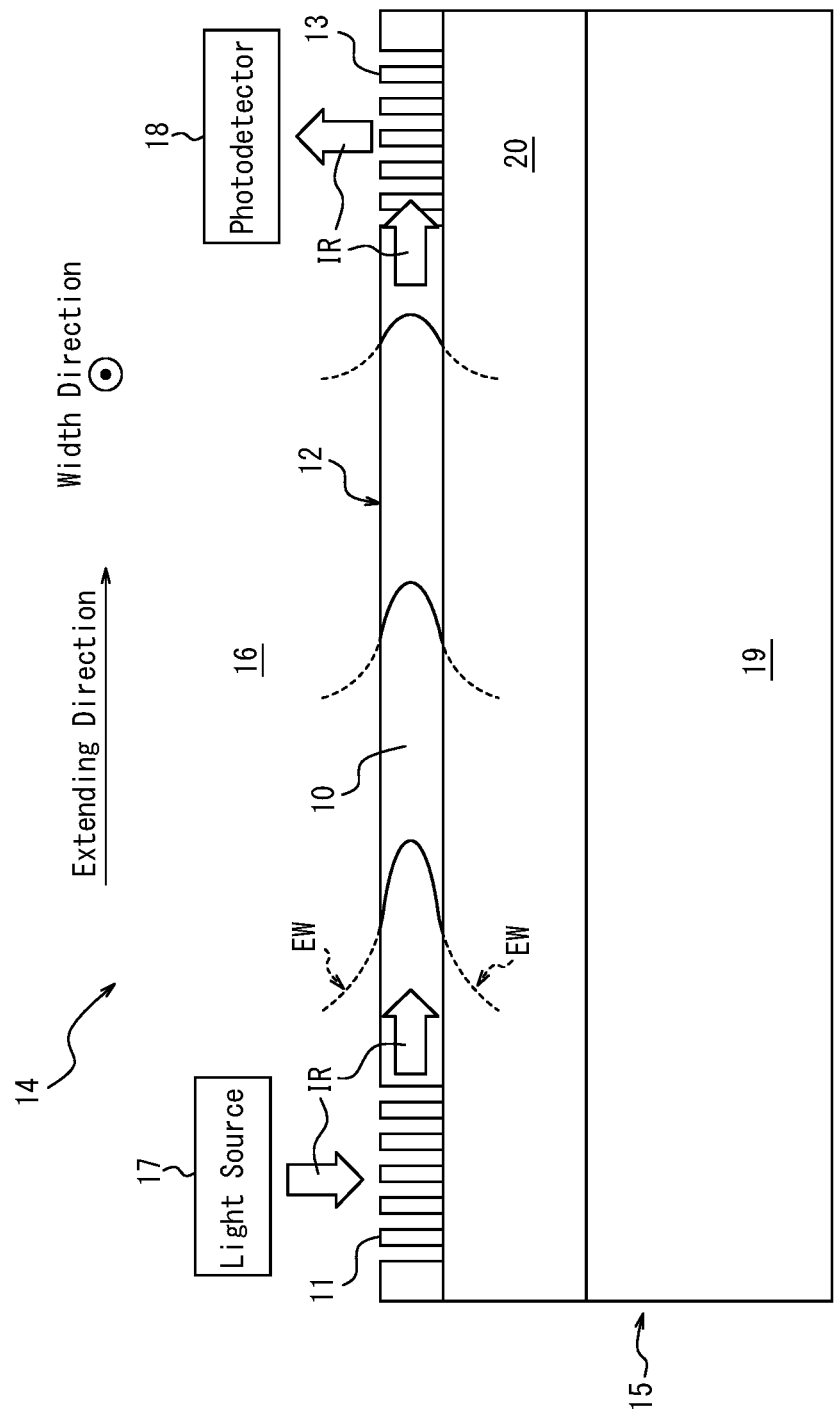
FIG. 1 illustrates the schematic configuration of an optical densitometer and an optical waveguide according to first and second embodiments of the present disclosure.

Embodiments of the present disclosure are now described, but the following embodiments do not limit the claimed subject matter. Furthermore, not all combinations of features described in the embodiments are necessarily essential to the solution to the problem of the present disclosure.

<Optical Densitometer>

An optical densitometer according to an embodiment of the present disclosure includes an optical waveguide, described below, according to an embodiment of the present disclosure, a light source capable of introducing light into a core layer, and a detector capable of receiving light propagating through the core layer.

The elements of the optical densitometer are described below with references to an example.

<Optical Waveguide>

An optical waveguide according to an embodiment of the present disclosure is an optical waveguide for use in an optical densitometer for measuring the density of a gas or liquid of interest. The optical waveguide includes a substrate, and a core layer including a light propagation portion through which light propagates in an extending direction of the light propagation portion, and a diffraction grating portion. Further, in the optical waveguide, the diffraction grating portion includes a diffraction grating region and an extension region connected to the diffraction grating region, and a first optical coupling region included in the extension region and a second optical coupling region included in the light propagation portion are optically coupled with respect to the light propagating through the core layer. Further, at least a portion of the diffraction grating portion may be spatially separated from the light propagation portion.

The optical waveguide according to the present embodiment enables the diffraction grating portion and the light propagation portion as the core layer to be formed in sizes and shapes, and from materials suited to their respective functions. In this configuration, the first optical coupling region included in the extension region and the second optical coupling region included in the light propagation portion are optically coupled with respect to the light propagating through the core layer. Accordingly, light introduced from the light source by the diffraction grating portion can be guided from the diffraction grating portion to the light propagation portion, or the light propagating through the light propagation portion can be introduced from the light propagation portion to the diffraction grating portion. In the first optical coupling region and the second optical coupling region, light propagating through the core layer optically couples from the first optical coupling region to the second optical coupling region, or from the second optical coupling region to the first optical coupling region.

In the present embodiment, the extending direction refers to at least one direction in which an object extends. For example, in a three-dimensional structure, the path of shortest distance from one end to another end (or any one point to any other point) while in contact with the three-dimensional structure is the extending direction. Alternatively, the direction that minimizes the change in cross-sectional area from one end to another end (or any one point to any other point) may be the extending direction. The extending direction need not be linear and may be curved.

Further, in the present embodiment, the extension region includes a portion which extends in the extending direction of the second optical coupling region which is included in the light propagation portion capable of propagating light. Specifically, one end thereof is connected to the diffraction grating region and the other end (end portion) is terminated without being connected to another core layer. The extension region connected to the diffraction grating region refers to the state in which the extension region and the diffraction grating region are formed of the same material as at least one of the materials of the layers forming the diffraction grating region, and is continuous with the at least one layer without being interrupted. The extension region is made from the material of that connecting portion inside the extension region.

Further, in the present embodiment, at least a portion of the diffraction grating portion is spatially separated from the light propagation portion means that a material (including the air) having a relatively lower refractive index than that of the core layer is interposed between the at least a portion of the diffraction grating portion and the light propagation portion.

Further, in the present embodiment, the diffraction grating portion including the extension region and the light propagation portion can be formed from any material. The diffraction grating portion and the light propagation portion may be formed from the same or different materials, but it is often preferable that they are formed from different materials. The reason is that in cases such as when the portion of the core layer separated from the diffraction grating portion is formed as a light propagation portion, the functions required for the diffraction grating portion differ from the functions required for the light propagation portion. Hence, forming these components from different materials enables materials to be chosen to suit the function required for each component and also allows the optical waveguide of the present embodiment to be manufactured more easily.

In the present disclosure, different materials refer not only to materials containing different elements, but also to materials in different crystalline state of the same element. This is because, in optical terms, light propagation phenomena differ if the crystal state differs, even if the constituent elements of the materials are the same.

In the present embodiment, the first optical coupling region included in the extension region and the second optical coupling region included in the light propagation portion are optically coupled with respect to light propagating through the core layer means that, when the light which has propagated to the extension region or the light propagation portion proceeds from the first optical coupling region to the second optical coupling region or from the second optical coupling region to the first optical coupling region, the light transitions to one to the other by using an evanescent wave or by causing the first optical coupling region and the second optical coupling region to come in direct contact with one another.

In the present embodiment, how the coupling of the first optical coupling region included in the extension region and the second optical coupling region included in the light propagation portion is established is not limited as long as they are optically coupled. Nevertheless, it is preferable that the propagation direction of the light propagating through the core layer does not substantially changes before and after the transition from the first optical coupling region to the second optical coupling region, and/or before and after the transition from the second optical coupling region to the first optical coupling region. In other words, in the present embodiment, the first optical coupling region and the second optical coupling region preferably function as a directional coupler for light propagating through the core layer. The first optical coupling region and the second optical coupling region functioning as a directional coupler can establish an ideal optical coupling with an efficiency of 100%. The first optical coupling region and the second optical coupling region functioning as a directional coupler refers to an optical coupled state in which light transitions from one to the other using an evanescent wave such that the propagation direction of light does not change before and after the transition.

In the present embodiment, the at least a portion of the diffraction grating portion may take any positional relationship with the light propagation portion as long as the first optical coupling region of the extension region and the second optical coupling region of the light propagation portion are optically coupled. For example, the extension region and the light propagation portion may be disposed in the optical waveguide so as to be adjacent to each other in the direction orthogonal to the extending direction of the light propagation portion (second optical coupling region). Alternatively, both at least a portion of the extension region and at least a portion of the light propagation portion may be disposed so as to be included in one plane orthogonal to the extending direction of the at least a portion of the light propagation portion. Further, in the case where the extension region and the light propagation portion are disposed so as to be adjacent to each other in the direction orthogonal to the extending direction of the light propagation portion, they may be disposed in the optical waveguide so as to be in the same position in the thickness direction, or so as to be in different positions in the thickness direction.

Among them, in the present embodiment, it is preferable the extension region and the light propagation portion are disposed so as to be adjacent to each other in the direction orthogonal to the extending direction of the light propagation portion, and to be separated in different positions in the thickness direction.

In the present embodiment, by separating the at least a portion of the diffraction grating portion and the light propagation portion from each other in the thickness direction, the diffraction grating portion and the light propagation portion having different functions will be located in different layers. In this structure, the diffraction grating portion and the light propagation portion can be efficiently subjected to processing suited to their respective functions. Further, it is possible to save the area in an efficient manner by grade-separating the diffraction grating portion and the light propagation portion. Further, even in the case where the at least a portion of the diffraction grating portion and the light propagation portion are provided so as to be separated from each other in the plane direction and to be disposed at the same portion in the thickness direction, the diffraction grating portion including the diffraction grating region and the extension region and the light propagation portion can be formed in different layers. This enables the diffraction grating portion and the light propagation portion to be subjected to processing suited to their respective functions.

Further, in the present embodiment, the distance between the first optical coupling region and the second optical coupling region is preferably equal to or smaller than the distance given by the following Expression (1):

$$\frac{3\lambda_0}{2\pi\sqrt{n_{coup}^2 - n_{mid}^2}} \quad \text{Expression (1)}$$

where $\lambda_0$ represents the average wavelength, in vacuum, of light propagating through the core layer, $n_{coup}$ represents the refractive index of the material forming the first optical coupling region or the second optical coupling region, and $n_{mid}$ represents the refractive index of a material present in the portion sandwiched between the first optical coupling region and the second optical coupling region. In the case where a plurality of materials are present in the portion sandwiched between the first optical coupling region and the second optical coupling region, the largest refractive index among the refractive indices of the plurality of materials is used as $n_{mid}$. This distance specifies a value three times the commonly-defined extending distance of evanescent light. The extending distance of the evanescent light refers to the distance, from the surface of the portion of the core layer in the thickness direction, of the position where the energy of light diminishes to 1/e from the energy value at the surface of the portion of the core layer. Therefore, the distance defined herein indicates the distance, from the surface of the portion of the core layer, of the position where the energy of light diminishes to $(1/e)^3$ or less from the energy value at the surface of the portion of the core layer. A distance between the first optical coupling region and the second optical coupling region of equal to or smaller than the distance given by above Expression (1) enables the first optical coupling region and the second optical coupling region to be optically coupled in no small extent. As the distance between the first optical coupling region and the second optical coupling region reduces, they can be coupled efficiently with a smaller area.

Note that the distance between the first optical coupling region and the second optical coupling region refers to the shortest distance among distances from points at the outer surface of the first optical coupling region facing the second optical coupling region, to the outer surface of the second optical coupling region. The lower limit of the distance between the first optical coupling region and the second optical coupling region is not particularly limited, and the first optical coupling region and the second optical coupling region may be in contact with each other. In the case where the first optical coupling region and the second optical coupling region are in direct contact with each other, $n_{mid}$ cannot be defined. In this case, the distance between the first optical coupling region and the second optical coupling region is 0 μm, which is regarded to be included in the range of equal to or smaller than the distance given by the above Expression (1).

Further, the distance between the first optical coupling region and the second optical coupling region is preferably 0.7 μm or smaller. For example, in an optical densitometer for detecting $CO_2$, which is a gas typically present in the environment, infrared radiation with a wavelength of approximately 4.3 μm in vacuum is typically used as the light to propagate through the core layer. In this case, the most common combination of materials forming the optical waveguide is a combination of silicon for the core layer and a silicon oxide film for the portion sandwiched between the first optical coupling region and the second optical coupling region. In this case, $n_{coup}$ is about 3.4, $n_{mid}$ is about 1.4, giving the value by the above Expression (1) of about 0.66 μm. In other words, the distance between the first optical coupling region and the second optical coupling region is 0.7 μm or smaller. For a more efficient optical coupling between the first optical coupling region and the second optical coupling region, the distance between the first optical coupling region and the second optical coupling region may be 0.4 μm or smaller, more preferably 0.2 μm or smaller, and even more preferably 0.1 μm or smaller. Alternatively, a silicon nitride film or any other material may be used as the material forming the portion sandwiched between the first optical coupling region and the second optical coupling region. In the case where a silicon nitride film is used, for example, $n_{mid}$ is about 2.0.

In the present embodiment, the refractive indices of the first optical coupling region and the second optical coupling region may have any values. Nevertheless, the equivalent refractive index of the first optical coupling region is preferably from 0.7 times to 1.3 times, more preferably from 0.8 times to 1.2 times, and even more preferably from 0.9 times to 1.1 times of the equivalent refractive index of the second optical coupling region, with respect to the light propagating through the core layer. When the equivalent refractive index of the first optical coupling region is from 0.7 times to 1.3 times of the equivalent refractive index of the second optical coupling region with respect to the light propagating through the core layer, the efficiency of the optical coupling improves as their equivalent refractive indices are closer.

Additionally, in the present embodiment, the refractive index of the material forming the first optical coupling region is preferably from 0.9 times to 1.1 times and more preferably from 0.95 times to 1.05 times of the refractive index of the material forming the second optical coupling region. When the refractive index of the material forming the first optical coupling region is from 0.9 times to 1.1 times of the refractive index of the material forming the second optical coupling region, the equivalent refractive index of the first optical coupling region becomes more likely to match the equivalent refractive index of the second optical coupling region with respect to the light propagating through the core layer as the refractive index of the material forming the first optical coupling region is closer to that of the material forming the second optical coupling region. This improves the efficiency of the optical coupling.

In the present embodiment, the film thickness of the first optical coupling region is preferably from 0.7 times to 1.3 times, more preferably from 0.8 times to 1.2 times, and even more preferably from 0.9 times to 1.1 times of the film thickness of the second optical coupling region. When the film thickness of the first optical coupling region is from 0.7 times to 1.3 times of the film thickness of the second optical coupling region, the equivalent refractive index of the first optical coupling region becomes more likely to match the equivalent refractive index of the second optical coupling region with respect to the light propagating through the core layer as the film thickness of the first optical coupling region is closer to that of the second optical coupling region. This improves the efficiency of the optical coupling.

In the present embodiment, the film thickness of the first optical coupling region and film thickness of the second optical coupling region refer to the respective film thicknesses of the first optical coupling region and the second optical coupling region in the region with the smallest distance between the first optical coupling region and the second optical coupling region in the case where the film thickness of the first optical coupling region varies in the first optical coupling region or the film thickness of the second optical coupling region varies in the second optical coupling region.

In the present embodiment, the width of the first optical coupling region is preferably from 0.7 times to 1.3 times, more preferably from 0.8 times to 1.2 times, and even more preferably from 0.9 times to 1.1 times of the width of the second optical coupling region. When the width of the first optical coupling region is from 0.7 times to 1.3 times of the width of the second optical coupling region, the equivalent refractive index of the first optical coupling region becomes more likely to match the equivalent refractive index of the second optical coupling region with respect to the light propagating through the core layer as the width of the first optical coupling region is closer to that of the second optical coupling region. This improves the efficiency of the optical coupling.

In the present embodiment, the width of the first optical coupling region and width of the second optical coupling region refer to the respective widths of the first optical coupling region and the second optical coupling region in the region with the smallest distance between the first optical coupling region and the second optical coupling region in the case where the width of the first optical coupling region varies in the first optical coupling region or the width of the second optical coupling region varies in the second optical coupling region.

In the present embodiment, preferably, the extension region is made from at least one of the materials forming the diffraction grating region, and is continuously connected to the diffraction grating region. Such a structure can prevent unintentional loss of light inside the diffraction grating portion.

Further, in the present embodiment, at least a portion of the light propagation portion is separated from the extension region preferably at a distance of greater than the distance between the first optical coupling region and the second optical coupling region, and more preferably at a distance greater than the distance given by the following Expression (2) or a distance greater than 0.7 μm:

$$\frac{3\lambda_0}{2\pi\sqrt{n_{pro}^2 - n_{gap}^2}} \qquad \text{Expression (2)}$$

where $\lambda_0$ represents the average wavelength, in vacuum, of light propagating through the core layer, $n_{pro}$ represents the refractive index of the material forming the light propagation portion or the extension region, and $n_{gap}$ is the refractive index of the material present in the portion sandwiched between the at least a portion of the light propagation portion and the extension region.

If the light propagation portion is in close proximity to the extension region except in the second optical coupling region, unintentional optical coupling occurs between the extension region and the light propagation portion. This unintentional optical coupling causes a transition from the extension region to the light propagation portion or a transition from the light propagation portion to the extension region, which results in loss of light. Thus, when at least a portion of the light propagation portion is separated from the extension region at a distance greater than the distance between the first optical coupling region and the second optical coupling region, unintentional optical coupling between the light propagation portion and the extension region is less likely to occur. Further, when the at least a portion of the light propagation portion is separated from the extension region at a distance greater than the distance given by Equation (2) or a distance greater than 0.7 μm, unintentionally optical coupling between the light propagation portion and the extension region is even less likely to occur. The reason why the distance with a smaller likelihood of optical coupling is specified by the Expression (2) is similar to the reason why the Expression (1) specifies the distance between the first optical coupling region and the second optical coupling region, and a detailed description thereof is omitted. The distance between the at least a portion of the light propagation portion and the extension region is defined as the shortest distance among distances between the outer surface of the at least a portion of the light propagation portion and the outer surface of the extension region.

Further, in the present embodiment, at least one of the light propagation portion and the extension region may include an end portion, and the distance between the end portion of the light propagation portion and the diffraction grating portion and/or the distance between the end portion of the extension region and the light propagation portion are preferably greater than the distance given by Expression (2)

or greater than 0.7 μm. Here, $n_{gap}$ shall be replaced with the refractive index of the material present in the portion sandwiched between the end portion of the light propagation portion and the diffraction grating portion, or the material present in the portion sandwiched between the end portion of the extension region and the light propagation portion. In the case where a plurality of materials are present in the portion sandwiched between the end portion of the light propagation portion and the diffraction grating portion or the portion sandwiched between the end portion of the extension region and the light propagation portion, the largest refractive index among the refractive indices of the plurality of materials is used as $n_{gap}$.

If the end portion of the light propagation portion is disposed in the vicinity of the diffraction grating portion, light which has propagated through the diffraction grating portion would encounter an abrupt change in the equivalent refractive index of the diffraction grating portion while it passes through the vicinity of the end portion of the light propagation portion, resulting in disturbances, such as reflection and scattering, of the light propagating through the diffraction grating portion. Similarly, if the end portion of the extension region is disposed in the vicinity of the light propagation portion, light which has propagated through the light propagation portion would encounter an abrupt change in the equivalent refractive index of the light propagation portion while it passes through the vicinity of the end portion of the extension region, resulting in disturbances, such as reflection and scattering, of the propagating light. Because these disturbances cause unintentional losses of the propagating light, the end portion of the light propagation portion and the diffraction grating portion, and/or the end portion of the extension region and the light propagation portion are preferably separated from each other at a certain distance. When the distance defined by Expression (2) or the distance of 0.7 μm is ensured, an evanescent wave of light propagating through the core layer of one of the light propagation portion and the diffraction grating portion is less likely to optically couple to the core layer of the other. The distance between the end portion of the light propagation portion and the diffraction grating portion is defined as the shortest distance among distances between the outer surface of the end portion of the light propagation portion and the outer surface of the diffraction grating portion. The distance between the end portion of the extension region and the light propagation portion is defined as the shortest distance among distances between the outer surface of the end portion of the extension region and the outer surface of the light propagation portion.

Further, in the present embodiment, in the region where the diffraction grating portion and the light propagation portion overlap in plan view, a first distance modification region may be provided in which the distance between the diffraction grating portion and the light propagation portion reduces in the direction approaching from the diffraction grating region toward the first optical coupling region. Further, the first distance modification region may have a portion in which the distance from the light propagation portion gradually changes from a distance greater than the distance given by Expression (2) or a distance greater than 0.7 μm, to a distance equal to or smaller than the distance given by Expression (1) or a distance of 0.7 μm or smaller. Here, $n_{gap}$ shall be replaced with the refractive index of the material present in the portion sandwiched between the light propagation portion and the at least a portion of the diffraction grating portion. In the case where a plurality of materials are present in the portion sandwiched between the light propagation portion and the at least a portion of the diffraction grating portion, the largest refractive index among the refractive indices of the plurality of materials is used as $n_{gap}$. Further, the maximum angle of the first distance modification region relative to the light propagation portion is preferably 45° or less.

In the region where the diffraction grating portion and the light propagation portion overlap in plan view, the first distance modification region in which the distance between the diffraction grating portion and the light propagation portion reduces in the direction approaching from the diffraction grating region toward the first optical coupling region provides a structure where the at least a portion of the diffraction grating portion approaches the light propagation portion gradually. This prevents propagating light from encountering an abrupt change in the equivalent refractive index of the at least a portion of the diffraction grating portion and the light propagation portion, thereby achieving an efficient optical coupling between the diffraction grating portion and the light propagation portion via the first optical coupling region and the second optical coupling region. Further, because the distance between the at least a portion of the diffraction grating portion and the light propagation portion gradually changes in the first distance modification region from a distance greater than the distance given by Expression (2) or a distance greater than 0.7 μm, to a distance equal to or smaller than the distance given by Expression (1) or a distance of 0.7 μm or smaller, an efficient optical coupling can be established between the first optical coupling region and the second optical coupling region while preventing unintentional optical coupling except in the first optical coupling region and the second optical coupling region. The distance between the at least a portion of the diffraction grating portion and the light propagation portion in the first distance modification region refers to the shortest distance among distances from points at the outer surface of the diffraction grating portion to the outer surface of the light propagation portion, in the first distance modification region.

Further, for achieving a reduction in loss of light in the first distance modification region, the maximum angle of the first distance modification region relative to the light propagation portion is preferably 45° or less and is more preferably 30° or less. If this angle is too small, on the other hand, the first distance modification region needs to be large (or long) for ensuring an appropriate distance between the at least a portion of the diffraction grating portion and the light propagation portion. Thus, the maximum angle of the first distance modification region relative to the light propagation portion is preferably 10° or more and more preferably 15° or more.

Further, in the optical waveguide, the substrate and the core layer may be separated from each other, and the distance L1 between the diffraction grating region and the substrate may differ from the distance L2 between the light propagation portion and the substrate.

In a conventional optical waveguide in which the distance L1 between the diffraction grating region and the substrate equals the distance L2 between the light propagation portion and the substrate, the optical waveguide is difficult to be designed to suppress leakage of an evanescent wave extending from the light propagation portion to the substrate while improving the diffraction efficiency of light in the diffraction grating region. According to the optical waveguide according to the present embodiment, the substrate and the core layer are separated from each other, and the distance L1 between the diffraction grating region and the substrate differs from the distance L2 between the light propagation portion and the substrate. It is thus possible to improve both the diffraction efficiency of light in the diffraction grating region and the propagation efficiency in the light propagation portion. Further, the distance L1 between the diffraction grating region and the substrate more preferably differs from the distance L2 between the light propagation portion and the substrate throughout the diffraction grating region.

Although the present embodiment is structured so that the first optical coupling region included in the extension region and the second optical coupling region included in the light propagation portion are optically coupled with respect to the light propagating through the core layer, the first optical coupling region and the second optical coupling region are not essential for controlling the distance L1 between the diffraction grating region and the substrate and the distance L2 between the light propagation portion and the substrate to differ from each other. Accordingly, the diffraction grating portion and the light propagation portion may be continuous so that no boundary can be distinguishable between the diffraction grating portion and the light propagation portion, as long as the distance L1 between the diffraction grating region and the substrate differs from the distance L2 between the light propagation portion and the substrate.

Further, in the present embodiment, the substrate and the core layer are separated means that a material (including the air) having a relatively lower refractive index than that of the core layer is interposed between the substrate and the core layer.

Further, in the present embodiment, the distance L1 between the diffraction grating region and the substrate refers to the length, measured in the thickness direction, from the surface of the diffraction grating region on the substrate side in the thickness direction, to the surface of the substrate on the diffraction grating region side in the thickness direction. The distance L2 between the light propagation portion and the substrate refers to the length, measured in the thickness direction, from the surface of the light propagation portion on the substrate side in the thickness direction, to the surface of the substrate on the light propagation portion side in the thickness direction.

Further, in the present embodiment, a support layer for supporting the core layer is preferably provided between the substrate and the core layer. The optical waveguide provided with the supporting layer can effectively separate the substrate and the core layer from each other.

In the present embodiment, the distance L2 between the light propagation portion and the substrate is preferably equal to or greater than a distance given by the following Expression (3):

$$\frac{6\lambda_0}{2\pi\sqrt{n_{pro}^2 - n_{L2}^2}} \quad \text{Expression (3)}$$

where $\lambda_0$ represents the average wavelength, in vacuum, of light propagating through the core layer, $n_{pro}$ represents the refractive index of the material forming the light propagation portion, and $n_{L2}$ represents the refractive index of the material present in the portion sandwiched between the light propagation portion and the substrate. In the case where a plurality of materials are present in the portion sandwiched between the light propagation portion and the substrate, the largest refractive index among the refractive indices of the plurality of materials is used as $n_{L2}$. This distance specifies a value six times the aforementioned extending distance of evanescent light. Therefore, the distance as specified herein specifies the distance, from the surface of the portion of the core layer, of the position where the energy of light diminishes to $(1/e)^6$ or less from the energy value at the surface of the portion of the core layer. The aforementioned maximum value of the distance between the first optical coupling region and the second optical coupling region has been specified to a value three times of the extending distance of evanescent light for achieving an optical coupling efficiently in a short distance. In contrast, the lower limit of the distance L2 between the light propagation portion and the substrate is for preventing an optical coupling between the light propagation portion and the substrate while light propagates over a long distance, and is thus specified to a value six times of the extending distance of evanescent light. If the distance L2 between the light propagation portion and the substrate is less than the value given by the above Expression (3), the light propagation portion and the substrate would be optically coupled relatively strongly. In a light propagation portion having a long propagation distance of several centimeters or longer, the amount of light leaking to the substrate generally tends to increase, which leads to a decrease in the propagation efficiency of the light propagation portion. By setting the distance L2 to be equal to or greater than the value given by the above Expression (3), leakage of an evanescent wave extending from the light propagation portion to the substrate can be suppressed to a sufficiently low level, thereby further improving the propagation efficiency of the light propagation portion.

The distance L2 between the light propagation portion and the substrate refers to the shortest distance among distances from points at the outer surface of the light propagation portion facing the substrate to the outer surface of the substrate.

The distance L2 between the light propagation portion and the substrate is preferably 1.3 µm or greater. For example, in an optical densitometer for detecting $CO_2$, which is a typical gas present in the environment, it is common to use an infrared radiation having a center wavelength of about 4.3 µm in vacuum as the light to propagate through the core layer. In this case, the most common combination of materials forming the optical waveguide is a combination of silicon for the core layer and the air for the portion sandwiched between the light propagation portion and the substrate. In this case, $n_{pro}$ is about 3.4, $n_{L2}$ is about 1.0, and the above Expression (3) gives a value of about 1.26 µm. Thus, 1.3 µm is the value equal to or greater than the value calculated from the above Expression (3). For more efficiently suppressing leakage of light propagating through the light propagation portion to the substrate, the distance L2 between the light propagation portion and the substrate may be 2.0 µm or greater, more preferably 2.5 µm or greater, and even more preferably may be 3.0 µm or greater. Alternatively, in the case where a silicon oxide film is used as the material forming the portion sandwiched between the light propagation portion and the substrate, $n_{L2}$ of about 1.4 is given.

In the present embodiment, in the case where the material forming a separation portion between the substrate and the diffraction grating region has a refractive index smaller than the refractive index of the substrate, the distance L1 between the diffraction grating region and the substrate preferably satisfies the following Expression (4):

$$\frac{(2m-1)\lambda_0 - 4n_{gr}t_{gr}}{4n_{L1}} - \frac{3\lambda_0}{16n_{L1}} \leq \quad \text{Expression (4)}$$

-continued $$L1 \leq \frac{(2m-1)\lambda_0 - 4n_{gr}t_{gr}}{4n_{L1}} + \frac{3\lambda_0}{16n_{L1}};$$

more preferably satisfies the following formula (5):

$$\frac{(2m-1)\lambda_0 - 4n_{gr}t_{gr}}{4n_{L1}} - \frac{\lambda_0}{8n_{L1}} \leq \quad \text{Expression (5)}$$

$$L1 \leq \frac{(2m-1)\lambda_0 - 4n_{gr}t_{gr}}{4n_{L1}} + \frac{\lambda_0}{8n_{L1}};$$

and even more preferably satisfies the following formula (6)

$$\frac{(2m-1)\lambda_0 - 4n_{gr}t_{gr}}{4n_{L1}} - \frac{\lambda_0}{16n_{L1}} \leq \quad \text{Expression (6)}$$

$$L1 \leq \frac{(2m-1)\lambda_0 - 4n_{gr}t_{gr}}{4n_{L1}} + \frac{\lambda_0}{16n_{L1}},$$

where $\lambda_0$ represents the average wavelength, in vacuum, of light propagating through the core layer, $n_{L1}$ represents the refractive index of the material forming the separation portion between the substrate and the diffraction grating region, $t_{gr}$ represents the effective film thickness of the diffraction grating region of the diffraction grating portion, $n_{gr}$ represents the refractive index of the material forming the diffraction grating region of the diffraction grating portion, and m is a natural number. In the case where a plurality of materials are present for forming the separation portion between the substrate and the diffraction grating region, the effective value calculated as $\{\Sigma(n_{L1i}^2 \times A_{L1i})\}^{1/2}$ is used as $n_{L1}$, where $n_{L1i}$ represents the refractive index of each material forming the isolation portion between the substrate and the diffraction grating region, and $A_{L1i}$ represents the occupation ratio of the each material between the substrate and the diffraction grating region. Further, the effective film thickness of the diffraction grating region of the diffraction grating portion is defined as a sum of the film thickness of the core layer in recessed portions of the diffraction grating region, and a half the film thickness difference of the core layer between recessed portions and protruding portions of the diffraction grating region. Further, in the case where a plurality of materials are present for forming the diffraction grating region of the diffraction grating portion, the effective value calculated as $\{\Sigma(n_{gri}^2 \times A_{gri})\}^{1/2}$ is used as $n_{gr}$, where $n_{gri}$ is the refractive index of each material forming the core layer in recessed portions of the diffraction grating region, and $A_{gri}$ represents the occupation ratio of the each material in the recessed portions of the diffraction grating region.

Light returns to its original phase when it travels an optical distance equivalent to an integer multiple of the wavelength of the light. Thus, when the distance L1 between the diffraction grating region and the substrate is an odd multiple of ¼ the wavelength, in the medium of the separation portion (between the substrate and the diffraction grating region), of light propagating through the core layer, the light that has taken one round trip of the distance L1 (i.e., light that is reflected by the surface of the substrate) can constructively interfere with light that has not traveled by the distance L1. It is presumed that the phase is displaced by half the wavelength when the light is reflected by the surface of the substrate. This phenomenon is described in R. M. Emmons and D. G. Hall, "Buried-Oxide Silicon-on-Insulator Structures II: Waveguide Grating Couplers", *IEEE JOURNAL OF QUANTUM ELECTRONICS*, VOL. 28, NO. 1, January 1992, pp. 164-175, for examples, as a technique to increase the efficiency of light extraction in a diffraction grating region. For extracting light to the outside by the diffraction grating region, however, a change in phase caused by propagation of light within the core layer forming the diffraction grating region also needs be taken into consideration. When such a phase change taken into consideration, the efficiency of light extraction to the outside by the diffraction grating region is maximized (details will be described below) when the distance L1 between the diffraction grating region and the substrate equals the distance given by the following Expression (7):

$$\frac{(2m-1)\lambda_0 - 4n_{gr}t_{gr}}{4n_{L1}}. \quad \text{Expression (7)}$$

In other words, the distance L1 between the diffraction grating region and the substrate has the optimum value at a period of a half the wavelength, in the medium of the separation portion (between the substrate and the diffraction grating region) (i.e., $\lambda_0/n_{L1}$), of light propagating through the core layer. Conversely, the efficiency reduces to the lowest when the value of L1 is the midpoint between the optimum value and the next optimum value, i.e., a distance at +/−¼ times of the wavelength, in the medium of the separation portion, of light propagating through the core layer with respect to the value given by the above Expression (7). It is thus possible to prevent the efficiency from reducing to the lowest by controlling the distance L1 to a distance within +/−3/16 times of the wavelength, in the medium of the separation portion, of light propagating through the core layer, with respect to the distance given by the above Expression (7). The distance L1 is controlled more preferably to a distance within +/−⅛ times of the wavelength, in the medium of the separation portion, of light propagating through the core layer, with respect to the distance given by the above Expression (7). The distance L1 is even more preferably controlled to a distance within +/−1/16 times of the wavelength, in the medium of the separation portion, of light propagating through the core layer, with respect to the distance given by the above Expression (7). By controlling the distance L1 to fall within one of the above ranges, the diffraction efficiency of light by the diffraction grating region can be maintained to a high level. Although the description has been given with reference to the case of extracting light to the outside in the diffraction grating region, the above principle is similarly applicable for cases of introducing light from the outside by the diffraction grating region.

Next, the elements of the optical waveguide are described below with references to examples.

<<Core Layer>>

In the present disclosure, the core layer includes a light propagation portion through which light propagates in an extending direction of the light propagation portion, and a diffraction grating portion.

The core layer is capable of propagating light in an extending direction of the core layer.

Any material may be used in the core layer. Examples of materials included in the core layer include monocrystalline silicon and polycrystalline silicon, amorphous silicon, silicon nitride, silicon germanium, germanium, gallium arsenide, indium phosphide, indium antimony, indium gallium arsenide, indium gallium phosphide, indium fluoride, diamond, sapphire, lithium niobate, and chalcogenide glass. The core layer may be a single-layered film or may be a multilayer film.

At least a portion of the diffraction grating portion may be formed from a material different from the material of the light propagation portion. In this case, the material forming the light propagation portion is preferably a monocrystalline material, and the material forming the diffraction grating portion preferably includes a polycrystalline or amorphous material. Most preferably, the material forming the light propagation portion is monocrystalline silicon, and the material forming the diffraction grating portion includes polycrystalline silicon or amorphous silicon.

By forming the respective core layers in the diffraction grating portion and the light propagation portion from different materials, the optimal core layers can be formed with the shapes, sizes, refractive indices, surface roughness, and the like, suited to the functions required for each core layer. Further, by forming the respective core layers in the diffraction grating portion and the light propagation portion from different materials, it is possible to independently process each core layer, and to process one core layer without being limited to conditions for the other core layer, which improves the degree of freedom of the processing.

More specifically, in the light propagation portion which is a portion for detecting the substance of interest, for example, the core layer is preferably formed so as to have a film thickness sufficiently smaller than the wavelength (the wavelength in the core layer) of light propagating through the core layer for increasing evanescent waves extending from the core layer. Additionally, a long propagation distance of light is required for improving the detection sensitivity of the substance of interest. In the light propagation portion intended to propagate light over a long distance, a monocrystalline material having a small surface roughness is preferred for the core layer for minimizing the propagation loss. The monocrystalline material which is the most common and is easy to process as the material of the core layer is monocrystalline silicon. Thus, the light propagation portion can be suitably formed at the lowest cost by forming the light propagation portion to include monocrystalline silicon.

On the other hand, in the diffraction grating portion which is a portion for introducing light from the light source into the core layer, the core layer preferably has a film thickness comparable to the wavelength (the wavelength in the core layer) of light propagating through the core layer for increasing the efficiency of entry of light. If the diffraction grating portion is too thin, entry of light into the core layer becomes extremely difficult. Additionally, the surface of the diffraction grating region of the diffraction grating portion is preferably provided with fine random irregularities (roughness). The reason is that the optical densitometer in the present embodiment detects the substance of interest by causing propagation of light with a wavelength band corresponding to the absorption spectrum of the substance of interest. The wavelength band of light to be propagated preferably matches a wavelength band in the absorption spectrum of the substance of interest. For example, when the diffraction grating region is formed to have a highly precise periodic pattern, light closer to single-wavelength light is selected by the diffraction grating region and the spectrum approaches a line spectrum. In other words, the selected wavelength band becomes narrower to approach a line spectrum, as the diffraction grating region is formed more precisely. The wavelength range of light absorption by a substance, however, has a certain width, and is not a strictly single wavelength. For example, a representative absorption wavelength of $CO_2$, which is a gas present in the environment, is distributed over a relatively wide range of approximately 4.20 μm to 4.35 μm. In other words, if light is excessively selected to the point of a strictly single wavelength, a wavelength effective for a density measurement is wasted. This is not preferable for an optical densitometer. In particular, the optical densitometer according to the present embodiment, as will be described later, can use an incoherent light source such as an LED as a light source. From the viewpoint of effectively utilizing light having a certain wavelength range (wavelength band) from an incoherent light source, the wavelength band selected by the diffraction grating region preferably has a certain width. In particular, in the present embodiment, the fine random irregularities (roughness) provided to the surface of the diffraction grating region of the diffraction grating portion increases the efficiency of coupling between the light-emitting element and the optical waveguide. By using a polycrystalline or amorphous material for the core layer forming the diffraction grating portion, provision of appropriate roughness on the surface of the core layer is facilitated. The polycrystalline or amorphous material which is the most common and easy to be processed for the core layer is polycrystalline silicon or amorphous silicon. Thus, by forming the diffraction grating portion so as to include polycrystalline silicon or amorphous silicon, the diffraction grating portion can be suitably formed at the lowest cost. Note that fine random irregularities (roughness) formed on the surface of the diffraction grating region are different from the periodic unevenness which define the diffraction grating region to be described later.

Furthermore, a cross-section orthogonal to the extending direction of the core layer at an arbitrary position along the extending direction may, for example, have a shape in which the distance from the center of the core layer to the outer surface in the cross-section varies, such as a rectangle, or a shape in which the distance from the center of the core layer to the outer surface in the cross-section does not vary, i.e. a circle.

In the present embodiment, at least a portion of the core layer may be exposed or covered by a thin film. Consequently, the portion of the core layer that is exposed or covered can come into direct contact with a gas or liquid of interest, or can come into contact with the gas or liquid of interest with the thin film interposed therebetween. This enables interaction between an evanescent wave and the gas or liquid of interest, thereby enabling measurement of the density of the gas or liquid of interest. In the present embodiment, the thin film is preferably thinner than ¼ the wavelength, in vacuum, of the light propagating through the core layer.

In the present embodiment, the light propagating through the core layer may be infrared radiation serving as an analog signal. Infrared radiation serving as an analog signal does not refer to determining the change in the energy of light to be one of two values, i.e. 0 (low level) or 1 (high level), but rather to a signal that carries the magnitude of change in the energy of light. The optical waveguide according to the present embodiment can therefore be used in sensors or analyzers. In this case, the wavelength, in vacuum, of the infrared light may be from 2 μm or greater to smaller than 12 μm. This is a wavelength band absorbed by gases ($CO_2$, CO, NO, $N_2O$, $SO_2$, $CH_4$, $H_2O$, $C_2H_6O$, and the like) that are typically present in the environment. This enables the optical waveguide according to each embodiment to be used as a gas sensor.

The core layer may include a portion extending in a curved shape. This enables the aspect ratio of the profile of the core layer to approach 1 in plan view of the entire core layer, enabling miniaturization of the optical waveguide and the optical densitometer.

Furthermore, as described above, the diffraction grating portion of the optical waveguide can include a first diffraction grating portion that receives light from a light source and guides the light towards the light propagation portion, and a second diffraction grating portion that receives the light from the light propagation portion and outputs the light to the detector.

In the present embodiment, as described above, the diffraction grating portion includes the diffraction grating region and the extension region, and a first optical coupling region included in the extension region and a second optical coupling region included in the light propagation portion are optically coupled with respect to the light propagating through the core layer. In the present embodiment, however, as long as one of the first diffraction grating portion and the second diffraction grating portion includes the diffraction grating region which is connected to the extension region including the first optical coupling region as described above, the other may be configured arbitrary, for example, so as not to include a diffraction grating region connected to the extension region including the first optical coupling region. Further, in the case where a plurality of diffraction grating regions are present in the first diffraction grating portion or a plurality of diffraction grating regions are present in the second diffraction grating portion, at least one of these the diffraction grating regions may be connected to the extension region including the first optical coupling region and the remaining diffraction grating regions may not be connected to the extension region including the first optical coupling region.

<<<Light Propagation Portion>>>

In the present embodiment, the light propagation portion has a propagation channel capable of propagating light in the extending direction of the light propagation portion. A cross-section orthogonal to the extending direction of the propagation channel at an arbitrary position along the extending direction may, for example, have a shape in which the distance from the center of the core layer to the outer surface in the cross-section varies, such as a rectangle, or a shape in which the distance from the center of the core layer to the outer surface in the cross-section does not vary, i.e. a circle.

The propagation channel in the present embodiment may have a substantially uniform film thickness in the extending direction. A substantially uniform film thickness refers, for example, to the height difference in the film thickness being 200 nm or smaller. The propagation channel may have a portion with a different width along the extending direction. In the case where the light propagation portion includes a plurality of propagation channels, the propagation channels may have different film thicknesses or widths. The film thickness of the core layer may or may not be uniform throughout the light propagation portion.

Further, the light propagation portion may be a multilayer film, but the light propagation portion preferably a single-layered film. This is because propagation loss may be increased in the light propagation portion which is a multilayer film because of a transition of light from one layer to another layer or conversion between propagation modes.

<<<Diffraction Grating Portion>>>

In the present embodiment, the diffraction grating portion can include a first diffraction grating portion that receives light from a light source and guides the light towards the light propagation portion, and a second diffraction grating portion that receives the light from the light propagation portion and outputs the light to the detector.

In the present embodiment, the first diffraction grating portion may include a light diffraction grating region that causes light from the outside to enter the core layer, and the second diffraction grating portion may include a light diffraction grating region that extracts light to outside the core layer. In the present embodiment, these light diffraction grating regions may be portions where an unevenness is formed on the surface over a particular period (or a plurality of periods). Alternatively, in a cross-sectional view of the optical waveguide including a plane having recessed portions and protruding portions, the recessed portions of the unevenness may become deep grooves, separating the core layer. In this configuration, the protruding portions are formed discontinuously.

The diffraction grating region can be provided so that, in plan view, unevenness is formed in parallel patterns extending as lines or arcs, but the unevenness may extend in any shape. Note that the diffraction grating region provided in the diffraction grating portion is partitioned as a region having the unevenness formed therein. In particular, the diffraction grating region provided in the diffraction grating portion is the region inside the portion between the outermost wall surfaces of at least either of the outer walls defining the protruding portions and the inner walls defining the recessed portions.

Further, in the present embodiment, the diffraction grating region may have any shape in plan view, and may have a shape having a portion which widens from the extension region side of the diffraction grating region toward the distal end opposite to the extension region, for example. Specific examples include a fan shape which has the center within the extension region of the diffraction grating portion and widens toward the distal end opposite to the extension region. The shape of the diffraction grating region preferably is line-symmetric relative to a virtual line extending from the extension region side towards the distal end.

In the present embodiment, the structure of the second diffraction grating portion may be the same structure as the first diffraction grating portion or a converted structure from the first diffraction grating portion. The converted structure from the first diffraction grating portion refers to that the shape, configuration, arrangement, and the like, of the diffraction grating region included in the second diffraction grating portion is a form with rotation, enlargement, reduction, translation, line symmetry, or point symmetry relative to the shape, configuration, arrangement, and the like, of the diffraction grating region included in the first diffraction grating portion. Noted that a difference between these structures within the wavelength, in vacuum, of light propagating through the core layer, preferably a difference of 1 µm or smaller, is tolerated. When the structure of the second diffraction grating portion is the same structure as the first diffraction grating portion or a converted structure from the first diffraction grating portion, the wavelength selectivity in the first diffraction grating portion and the wavelength selectivity in the second diffraction grating portion can be made substantially equivalent. This can avoid light loss occurring when the wavelength selectivities differ between the first diffraction grating portion and the second diffraction grating portion.

<<Substrate>>

The substrate in the present embodiment may be any substrate on which the core layer can be formed. The below-described support layer can also be formed on the substrate. Specific examples of the substrate include a silicon substrate and a GaAs substrate.

<<Support Layer>>

Any support layer may be provided in the present embodiment. The support layer connects at least a portion of the substrate and at least a portion of the core layer. The support layer may be any material capable of joining the substrate and the core layer but is preferably a material that has a smaller refractive index than that of the core layer with respect to light of any wavelength or light propagating through the core layer. Examples of the material forming the support layer include $SiO_2$. The support layer is not an essential element in the present disclosure. The core layer may be joined to the substrate by the support layer, or the core layer may be formed directly on the substrate. The support layer may be discontinuous, and at least a portion of the core layer may be free-standing, without being joined to the support layer. In other words, a space is provided between the substrate and the core layer except in a region where the support layer is provided in an optical waveguide configured in this way. The extent of the interaction between the evanescent wave and the substance of interest can be increased by causing a portion of the core layer to be free-standing. This can increase sensor sensitivity.

An example of a method of forming the support layer in the present embodiment is to etch a buried oxide (BOX) layer ($SiO_2$ layer) of an SOI substrate, thereby forming a structure in which the BOX layer supports the core layer (Si layer) with respect to the substrate (Si layer).

<Light Source>

The light source may be any light source capable of introducing light into the core layer. An incandescent bulb, a ceramic heater, a micro electro mechanical systems (MEMS) heater, an infrared light-emitting diode (LED), or the like can be used as the light source in the case of using infrared radiation to measure a gas. In other words, the light source may be an incoherent light source. The light source may be arranged in any way that allows an optical coupling. For example, the light source may be arranged adjacent to the optical waveguide in the same part as the optical waveguide or may be arranged in a separate part separated from the optical waveguide at a certain distance. A mercury lamp, an ultraviolet LED, or the like can be used as the light source in the case of using ultraviolet rays to measure a gas.

The light propagating through the core layer of the optical waveguide provided in the optical densitometer may be infrared radiation serving as an analog signal. Infrared radiation serving as an analog signal does not refer to determining the change in the energy of light to be one of two values, i.e. 0 (low level) or 1 (high level), but rather to a signal that carries the magnitude of change in the energy of light. The optical densitometer can therefore be applied to sensors or to analyzers. In this case, the wavelength of the infrared light may be from 2 µm or greater to smaller than 12 µm. This is a wavelength band absorbed by gases ($CO_2$, CO, NO, $N_2O$, $SO_2$, $CH_4$, $H_2O$, $C_2H_6O$, and the like) that are typically present in the environment. This makes the optical densitometer of the present embodiment to be used as a gas sensor.

<Detector>

The detector may be any detector capable of receiving the light that has propagated through the core layer of the optical waveguide. A thermal infrared sensor such as a pyroelectric sensor, a thermopile, or a bolometer; a quantum infrared sensor such as a diode or a phototransistor; or the like can be used as the detector in the case of using infrared radiation to measure a gas. A quantum ultraviolet sensor, such as a diode or a phototransistor, or the like can be used as the detector in the case of using ultraviolet rays to measure a gas.

[Optical Densitometer According to Embodiment of the Present Disclosure]

An optical densitometer according to an embodiment of the present disclosure is described with reference to FIG. 1.

An optical densitometer 14 according to this embodiment is installed and used in an exterior space 16 containing a gas whose density or the like is to be detected. The optical densitometer 14 of the present embodiment includes an optical waveguide 15 of an embodiment, described below, a light source 17 capable of introducing light into a core layer 12, and a photodetector 18 capable of receiving the light that has propagated through the core layer 12. Further, the optical densitometer 14 includes a first diffraction grating portion 11 that receives light from the light source 17 and guides the light to a light propagation portion 10, and further includes a second diffraction grating portion 13 that receives light from the light propagation portion 10 and guides the light to the photodetector 18.

The light source 17 in the optical densitometer 14 of the present embodiment emits infrared radiation with a wavelength of 2 µm or greater and smaller than 12 µm toward the core layer 12. As a result of using this infrared radiation, an evanescent wave EW extending from the core layer 12 is absorbed by a substance of interest that is present in the exterior space 16, such as $CO_2$, CO, NO, $N_2O$, $SO_2$, $CH_4$, $H_2O$, $C_2H_6O$, or another gas. The density of the substance of interest can thus be detected.

Note that the optical densitometer 14 of the present embodiment is obtained by first manufacturing the below-described optical waveguide 15 according to an embodiment of the present disclosure. Subsequently, the light source 17 is installed to be capable of introducing infrared radiation IR into one diffraction grating portion 11 (grating coupler) of the optical waveguide 15, and the photodetector 18 is disposed to be capable of receiving the infrared radiation IR emitted from the other diffraction grating portion 13 (grating coupler) of the optical waveguide 15, as illustrated in FIG. 1.

[Optical Waveguide According to Embodiments of the Present Disclosure]

First Embodiment

An optical waveguide according to a first embodiment of the present disclosure is described with reference to FIGS. 1 through 3.

FIG. 1 illustrates the schematic configuration of the optical densitometer 14 according to the first embodiment and a second embodiment, described later, and is also a conceptual drawing of the ATR technique using an optical waveguide 15 according to the first or second embodiment.

The optical waveguide 15 includes a substrate 19, a core layer 12 through which the infrared radiation IR (an example of light) can propagate, and a support layer 20 configured to connect at least a portion of the substrate 19 with at least a portion of the core layer 12 and support the core layer 12 with respect to the substrate 19. The core layer 12 and the substrate 19 are, for example, formed from silicon (Si), and the support layer 20 is, for example, formed from silicon dioxide ($SiO_2$). The substrate 19 and the support layer 20 are, for example, plate-shaped. The support 20 may support the entire core layer 12, as illustrated in FIG. 1, or may support at least a portion of the core layer 12. For example, the support 20 can be configured to support the entire diffraction grating portions 11 and 13 and a portion of the light propagation portion 10 discontinuously in the extending direction. In the resulting optical waveguide 15, the light propagation portion 10 is connected to the support layer 20 discontinuously in the extending direction, and a gap without a certain layer, such as a cladding layer, is present between the light propagation portion 10 and the substrate 19, except in the regions where the support 20 is provided.

The core layer 12 includes a first diffraction grating portion (grating coupler as one example) 11 formed at one end in the extending direction and a second diffraction grating portion (grating coupler as an example) 13 formed at the other end, as illustrated in a schematic diagram illustrating the schematic configuration of the optical waveguide 15 in FIG. 2. The core layer 12 includes the light propagation portion 10 between the first diffraction grating portion 11 and the second diffraction grating portion 13 disposed at the respective ends in the extending direction. The film thickness of the light propagation portion 10 in the optical waveguide 15 according to the first embodiment is uniform. The width of the light propagation portion 10 in the optical waveguide 15 according to the first embodiment is also uniform. The width direction is the direction orthogonal to the extending direction and the thickness direction. The thickness direction is the direction parallel to the stacking direction in which the substrate 19, support layer 20, and the core layer 12 are stacked.

The first diffraction grating portion 11 is disposed in the emission direction of the light source 17. In the first embodiment, the optical waveguide 15 is arranged so that the stacking direction thereof is parallel to the vertical direction, and the principal surface of the substrate 19 is in a direction orthogonal to vertical direction and is in the vertically downward from the light source 17. The principal surface of the substrate 19 is a surface orthogonal to the thickness direction of the substrate 19 and refers, in the first embodiment, to the surface with the largest area among the six surfaces forming the substrate 19. In other words, the emission direction of the light source 17 is the vertically downward direction from the light source 17 when the optical waveguide 15 is installed in this manner. This first diffraction grating portion 11 is configured to introduce the infrared radiation IR emitted from the light source 17 to the core layer 12. Accordingly, the light that is to propagate through the core layer 12 is entered from the thickness direction of the first diffraction grating portion 11. The second diffraction grating portion 13 is disposed in the direction facing the photodetector 18. The direction facing the photodetector 18 is the vertically downward direction from the photodetector 18 when the optical waveguide 15 is installed in the above-described manner. This second diffraction grating portion 13 is configured to extract the infrared radiation IR propagating through the core layer 12 and emit the infrared radiation IR towards the photodetector 18. Accordingly, the light that has propagated through the core layer 12 is output in the thickness direction of the second diffraction grating portion 13.

In this way, the first diffraction grating portion 11 is provided at one end of the core layer 12 disposed on the light source 17 side (light introduction side), and the second diffraction grating portion 13 is provided at the other end of the core layer 12 disposed on the photodetector 18 side (light emission side). The light propagation portion 10 extends from the center of the core layer 12 toward the two ends in the extending direction, and the infrared radiation IR introduced from the first diffraction grating portion 11 propagates through the light propagation portion 10 and is emitted from the second diffraction grating portion 13. An evanescent wave EW extending from the core layer 12 is primarily absorbed by the substance of interest present in the exterior space 16 around or near the light propagation portion 10.

The optical waveguide 15 according to the first embodiment is now described in greater detail.

As illustrated in FIG. 1, a sensor employing the ATR technique can improve the sensitivity of the sensor by expanding the region of interaction between an evanescent wave EW extending from the core layer 12 and a substance of interest (i.e. by expanding the exposed portion of the core layer 12). Furthermore, in a sensor employing the ATR technique, the light introduced into the core layer needs to extend from a light propagation portion 10 as an evanescent wave and be absorbed by the external substance of interest, as described above. A long propagation distance of light through the light propagation portion 10 (propagation channel 101) is therefore required. The diffraction grating portions for inputs or outputs of light are also required to be structured so as to suit the sizes and shapes of the light source and the photodetector in view of efficient light inputs to the optical waveguide or efficient light outputs from the optical waveguide. In such a sensor, therefore, the required functions of the diffraction grating portions and the light propagation portion 10, which are all core layers, differ from each other, and it is desirable to form them in the sizes, shapes, and materials to suit the respective functions.

To meet the needs, in the optical waveguide 15 according to the first embodiment, as illustrated in FIG. 3, the first diffraction grating portion 11 includes a diffraction grating region 111 and an extension region 111a connected to the diffraction grating region 111. The diffraction grating region 111 and the extension region 111a are all formed from a material different from the material of the light propagation portion 10, and are all spatially separated from the light propagation portion 10. A first optical coupling region 111b included in the extension region 111a and a second optical coupling region 101b included in the light propagation portion 10 are optically coupled with respect to light propagating through the core layer 12. In an example, the optical coupling surface between the first optical coupling region 111b and the second optical coupling region 101a is not orthogonal to the principal surface of the substrate 19. For example, the optical coupling surface may be parallel to the principal surface of the substrate 19. Although not illustrated, the second diffraction grating portion 13 similarly includes a diffraction grating region 131 and an extension region 131a connected to the diffraction grating region 131. The diffraction grating region 131 and the extension region 131a are all spatially separated from the light propagation portion 10. A first optical coupling region 131b included in the extension region 131a and a second optical coupling region 101a included in the light propagation portion 10 are optically coupled with respect to light propagating through the core layer 12.

Accordingly, in the optical waveguide 15 according to the first embodiment, the diffraction grating regions 111, 131 and the extension regions 111a, 131a connected to the diffraction grating regions 111, 131 are all formed from a material different from the material of the light propagation portion 10, and are all spatially separated from the light propagation portion 10. Thus, the first diffraction grating portion 11, the second diffraction grating portion 13, and the light propagation portion 10 as the core layer 12 can be formed so as to have sizes and shapes, and be formed from materials suited to their respective functions. In this structure, the first optical coupling regions 111b, 131b included in the extension regions 111a, 131a and the second optical coupling regions 101a included in the light propagation portion 10 are optically coupled with respect to light propagating through the core layer 12. This ensures that light from the light source received by the first diffraction grating portion 11 is guided from the first diffraction grating portion 11 to the light propagation portion 10, and light which has propagated through the light propagation portion 10 is guided from the light propagation portion 10 to the second diffraction grating portion 13.

Here, in the optical waveguide 15 according to the first embodiment, the couplings of the first optical coupling regions 111b, 131b included in the extension regions 111a, 131a and the second optical coupling region 101a included in the light propagation portion 10 are not particularly limited as long as they are optically coupled with respect to the light propagating through the core layer 12 (specifically, the first optical coupling regions 111b, 131b and the second optical coupling regions 101a). Nevertheless, as illustrated in FIG. 3, the first optical coupling regions 111b, 131b and the second optical coupling regions 101a are preferably disposed in the direction orthogonal to the extending direction of the light propagation portion 10, which makes the extension regions 111a, 131a and the light propagation portions 10 function as directional couplers. By making them function as directional couplers, efficient optical couplings therebetween are established.

Specifically in the optical waveguide 15 according to the first embodiment, as illustrated in FIG. 2, each of the first diffraction grating portion 11 and the second diffraction grating portion 13 includes one diffraction grating region 111, 131, and the light propagation portion 10 including one propagation channel 101 extends between the first diffraction grating portion 11 and the second diffraction grating portion 13. The first diffraction grating portion 11 and the second diffraction grating portion 13 include respective extension regions 111a, 131a, as illustrated in FIG. 3 (illustration of the second diffraction grating portion 13 is omitted), and each of the extension regions 111a, 131a is made of the same material as one of the materials forming the diffraction grating regions 111, 131. In addition, the diffraction grating regions 111, 131 and the extension regions 111a, 131a are all made from a material different from the material of the propagation channel 101 of the light propagation portion 10, and are all separated from the propagation channel 101 of the light propagation portion 10. Further, the extension regions 111a, 131a include the first optical coupling regions 111b, 131b, respectively. The propagation channel 101 has second optical coupling regions 101a in the vicinity of the respective ends of the propagation channel 101. The first optical coupling regions 111b, 131b and the corresponding second optical coupling regions 101a are optically coupled with respect to light propagating via the first optical coupling regions 111b, 131b and the second optical coupling regions 101a.

Further, in the optical waveguide 15 according to the first embodiment, specifically as illustrated in FIG. 3B, each extension region 111a, 131a and the light propagation portion 10 are disposed so as to be separated from each other in the direction orthogonal to the extending direction of the light propagation portion 10 and at positions different from each other in the thickness direction (in the illustrated example, the light propagation portion 10 is positioned on the substrate side in the thickness direction relative to the extension region 111a). In other words, the extension region 111a, 131a and the light propagation portion 10 overlap each other in the extending direction of the light propagation portion 10, and are disposed in the different layers. By disposing the extension region 111a, 131a and the light propagation portion 10 at positions different from each other in the thickness direction so as to be separated from each other in the direction orthogonal to the extending direction of the light propagation portion 10, portions which have different functions and form the core layer 12 are disposed in the different layers. In addition, the first diffraction grating portion 11, the second diffraction grating portion 13, and the light propagation portion 10 can be efficiently processed so as to suit to the respective functions.

In the optical waveguide 15 according to the first embodiment, the extension region 111a of the first diffraction grating portion 11 and the extension region 131a of the second diffraction grating portion 13, and the light propagation portion 10 may have any positional relationships as long as the first optical coupling regions 111b, 131b included in the extension regions 111a, 131a and the corresponding second optical coupling regions 101a included in the light propagation portion 10 are optically coupled. Unlike FIG. 3, the extension regions 111a, 131a and the light propagation portion 10 can be provided at the same position in the thickness direction in the optical waveguide 15 so as to be separated from each other in the planar direction.

Although the extension regions 111a, 131a and the light propagation portion 10 extend so as to be separated from each other in the example depicted in FIG. 3, the extension regions 111a, 131a and the light propagation portion 10, more specifically, the first optical coupling regions 111b, 131b and the second optical coupling regions 101a, may be in contact with each other.

In the optical waveguide 15 according to the first embodiment, the shapes of the extension regions 111a, 131a are not particularly limited. For example, as illustrated in FIG. 3A, one end of the extension region 111a of the first diffraction grating portion 11 is continuously connected to the diffraction grating region 111 without being interrupted, and the other end (end portion) is terminated without being connected to another core layer 12 (illustration of the second diffraction grating portion 13 is omitted). Further, as illustrated in the cross-sectional view (in the illustrated example, the cross-sectional view in the thickness direction as illustrated in FIG. 3B) including the first optical coupling regions 111b, 131b of the extension regions 111a, 131a and the second optical coupling regions 101a of the propagation channel 101, the extension regions 111a, 131a have first distance modification regions 111c, 131c which are curved toward the propagation channel 101 so that the first optical coupling regions 111b, 131b included in the extension regions 111a, 131a and the corresponding second optical coupling regions 101a of the propagation channel 101, which are portions to be optically coupled, approach each other. In the first distance modification regions 111c, 131c (i.e., curved portions), the distance from the propagation channel 101 gradually changes from a distance at which the extension region 111a and the propagation channel 101 are less likely to be optically coupled (a distance greater than the distance given by Equation (2) or a distance greater than 0.7 µm), to a distance at which an optical coupling is established (a distance equal to or smaller than the distance given of Equation (1) or a distance of 0.7 µm or smaller). Here, $n_{gap}$ is the refractive index of the material present in the portion sandwiched between the propagation channel 101 and the first distance modification region 111c, 131c. The first distance modification regions 111c, 131c are continuous with the first optical coupling regions 111b, 131b, respectively. For preventing loss of light, the maximum angle relative to the principal surface of the substrate 19 of the curved portions is preferably 45° or less and more preferably 30° or less. If the angle is too small, on the other hand, a great distance is required for making the first optical coupling region 111b, 131b and the second optical coupling region 101a approach each other. Thus, the maximum angle of the curved portions is preferably 10° or more and more preferably 15° or more relative to the principal surface of the substrate 19.

Further, the propagation channel 101 and the extension region 111a, 131a have portions which extend parallel to each other in plan view. In other words, the extension region 111a, 131a has a first distance modification region 111c, 131c that is curved so that the distance between the extension region 111a, 131a and the propagation channel 101 gradually decreases to a distance at which the extension region 111a, 131a and the propagation channel 101 are optically coupled, from one end of the extension region 111a, 131a (connecting portion with the diffraction grating region 111, 131) toward the other end (end portion). The extension region 111a, 131a then includes a portion in which the extension region 111a, 131a (first optical coupling region 111b, 131b) extends spaced apart from the propagation channel 101 (second optical coupling region 101a) at a constant distance, in the first optical coupling region 111b, 131b. The extension region 111a, 131a further includes a second distance modification region 111d, 131d which is curved so that the distance between the extension region 111a, 131a and the propagation channel 101 gradually increases, and finally terminates at the other end (end portion).

In the above example, the propagation channel 101 has the end portion, and the second optical coupling region 101a is disposed so as to be separated from the end portion of the propagation channel 101 (light propagation portion 10). The second optical coupling region 101a, however, may be disposed at the end portion of the propagation channel 101 (light propagation portion 10). The second optical coupling region 101a, however, is preferably disposed so as to be separated from the end portion of the propagation channel 101, rather than being disposed at the end portion of the propagation channel 101. By disposing the second optical coupling region 101a so as to be separated from the end portion of the propagation channel 101, as illustrated in FIG. 3B, the respective distances between the end portion of the propagation channel 101 and the first diffraction grating portion 11 or the second diffraction grating portion 13 can be set to a distance at which they are less likely to be optically coupled (a distance greater than the distance given by Equation (2) or a distance greater than 0.7 μm). Here, $n_{gap}$ represents the refractive index of the material present in the portion sandwiched between the end portion of the propagation channel 101 and the first diffraction grating portion or the second diffraction grating portion.

In other words, in the above example, the propagation channel 101 is separated from the first diffraction grating portion 11 or the second diffraction grating portion 13 in the thickness direction at a distance at which an optically coupling is less likely to be established (at a distance greater than the distance given by Expression (2) or a distance greater than 0.7 μm), except in the second optical coupling regions. Here, $n_{gap}$ is the refractive index of a material present in the portion sandwiched between the portion other than the second optical coupling regions of the propagation channel 101 and the first diffraction grating portion 11 or the second diffraction grating portion 13.

Further, in the first embodiment, the first optical coupling regions 111b, 131b can be disposed at any positions in the extension regions 111a, 131a. The first optical coupling regions 111b, 131b may be positioned at the respective end portions of the extension regions 111a, 131a. As illustrated in FIG. 3B and described above, the first optical coupling region 111b, 131b, however, is preferably located in the middle of the extension region 111a, 131a (between the first distance modification region 111c, 131c where the distance between the extension region 111a and the propagation channel 101 gradually decreases and the second distance modification region 111d, 131d where the distance gradually increases). In other words, the first optical coupling region 111b, 113b is preferably located between one end of the extension region 111a, 131a connected to the diffraction grating region 111, 131 and the other terminating end (end portion), so as to be separated from the ends. Because the first optical coupling region 111b, 131b is provided in the middle of the extension region 111a, 131a, as illustrated in FIG. 3B, the distance between the end portion of the extension region 111a and the propagation channel can be set to a distance at which they are less likely be optically coupled (a distance greater than the distance given by Equation (2) or a distance greater than 0.7 μm). Here, $n_{gap}$ is the refractive index of a material present in the portion sandwiched between the end portion of the extension region 111a and the propagation channel 101. Further, because the first optical coupling region 111b, 131b is provided in the middle of the extension region 111a, 131a, the end portion of the extension region 111a, 131a can be etched without damaging the propagation channel 101, thereby enabling an improvement in the propagation efficiency of light through the propagation channel 101.

In the first embodiment, the shapes of the extension regions 111a, 131a are not limited as long as they include at least the first optical coupling regions 111b, 131b.

In the first embodiment, the extension regions 111a, 131a and the light propagation portion 10 are separated from each other in the thickness direction, and a layer different from the extension regions 111a, 131a and the light propagation portion 10 is present between the extension regions 111a, 131a and the light propagation portion 10. A material (including the air) with a refractive index relatively lower than that of the core layer 12 (including the extension regions 111a, 131a and the light propagation portion 10) may be interposed between the extension regions 111a, 131a and the light propagation portion 10, and in the illustrated example, a silicon oxide film ($SiO_2$) is present between the first diffracting grating portion 11 and the light propagation portion 10.

In the first embodiment, the distance between the first optical coupling region 111b, 131b and the second optical coupling region 101a is preferably equal to or smaller than the distance given by above Expression (1) or equal to or less than 0.7 μm. Here, Xo represents the average wavelength, in vacuum, of light propagating through the core layer, $n_{coup}$ is the refractive index of the material forming the first optical coupling region 111b, 131b or the second optical coupling region 101a, and $n_{mid}$ is the refractive index of the material present in the portion sandwiched between the first optical coupling region 111b, 131b and the second optical coupling region 101a. Because the distance between the first optical coupling region 111b, 131b and the second optical coupling region 101a is set within the above-mentioned range, the first optical coupling region 111b, 131b and the second optical coupling region 101a can be optically coupled efficiently at the short distance (length in extending direction).

Further, the length of the optical coupling between the first optical coupling region 111b, 131b and the second optical coupling region 101a in the extending direction is preferably 20 μm or smaller and more preferably 10 μm or smaller. When the length is within one of the above-described ranges, the first optical coupling region 111b, 131b and the second optical coupling region 101a can be optically coupled in a space-saving manner. The length of the optical coupling between the first optical coupling region 111b, 131b and the second optical coupling region 101a in the extending direction refers to the length of the portion in which the distance between the extension region 111a, 131a and the propagation channel 101 is equal to or smaller than the distance given by above Expression (1) or equal to or less than 0.7 μm, i.e., the length of the portion defined as the first optical coupling region 111b, 131b and the second optical coupling region 101a.

The diffraction grating portions 11, 13 including the extension regions 111a, 131a and the light propagation portion 10 can be formed from any material in the first embodiment. In the illustrated example, the diffraction grating portions 11, 13 and the light propagation portion 10 are formed from different materials. The functions required for the diffraction grating portions 11, 13 differ from those of the light propagation portion 10. When they are formed from different materials, materials that are suited to the functions required for the respective components can be selected and the optical waveguide can be manufactured more suitably.

In the illustrated example, the material of the diffraction grating portions 11, 13 is polycrystalline silicon and the material of the light propagation portion 10 is monocrystalline silicon. Alternatively, an amorphous silicon material may be used as the material for forming the diffraction grating portions 11, 13 or the light propagation portion 10.

Further, in the first embodiment, the equivalent refractive index of the first optical coupling regions 111b, 131b is preferably from 0.7 times to 1.3 times, more preferably from 0.8 times to 1.2 times, and more preferably from 0.9 times to 1.1 times of the equivalent refractive index of the second optical coupling regions 101a, with respect to light propagating through the first optical coupling regions 111b, 131b and the second optical coupling regions 101a. As the equivalent refractive index of the first optical coupling regions 111b, 131b becomes closer to that of the second optical coupling regions 101a with respect to light propagating through the first optical coupling regions 111b, 131b and the second optical coupling regions 101a, the efficiency of an optical coupling therebetween is increased.

Further, in the first embodiment, the refractive index of the material forming the first optical coupling regions 111b, 131b is preferably from 0.9 times to 1.1 times and more preferably from 0.95 times to 1.05 times of the refractive index of the material forming the second optical coupling regions 101a. As the refractive index of the material forming the first optical coupling regions 111b, 131b becomes closer to that of the material forming the second optical coupling regions 101a, the equivalent refractive index of the first optical coupling regions 111b, 131b is more likely to match that of the second optical coupling regions 101a with respect to light propagating through the first optical coupling regions 111b, 131b and the second optical coupling regions 101a. This improves the efficiency of the optical coupling.

Further, in the first embodiment, the film thicknesses of the extension regions 111a, 131a and the film thickness of the propagation channel 101 may be set to any values. Nevertheless, as illustrated in FIG. 3B, the film thicknesses of the first optical coupling regions 111b, 131b are preferably from 0.7 times to 1.3 times, more preferably from 0.8 times to 1.2 times, and more preferably from 0.9 times to 1.1 times of the film thicknesses of the second optical coupling regions 101a. More specifically, the film thicknesses of the extension regions 111a, 131a including the first optical coupling regions 111b, 131b are preferably from 0.7 times to 1.3 times, more preferably from 0.8 times to 1.2 times, and more preferably from 0.9 times to 1.1 times of the film thickness of the propagation channel 101 including the second optical coupling regions 101a. As the film thicknesses of the first optical coupling regions 111b, 131b become closer to those of the second optical coupling regions 101a, the equivalent refractive index of the first optical coupling regions 111b, 131b is more likely to match that of the second optical coupling regions 101a with respect to light propagating through the first optical coupling regions 111b, 131b and the second optical coupling regions 101a. This improves the efficiency of the optical coupling.

In the first embodiment, the film thicknesses of the first optical coupling regions 111b, 131b and the film thicknesses of the second optical coupling regions 101a refer to the respective film thicknesses in the portions where the respective distances between the first optical coupling regions 111b, 131b and the second optical coupling regions 101a become the smallest in the case where the film thicknesses of the first optical coupling regions 111b, 131b vary in the first optical coupling regions 111b, 131b or the film thicknesses of the second optical coupling regions 101a vary in the second optical coupling regions 101a.

The film thicknesses of the first optical coupling regions 111b, 131b and the second optical coupling regions 101a are preferably from 0.2 μm to 1.0 μm in view of manufacturing and the optical properties.

Further, in the first embodiment, the widths of the extension regions 111a, 131a and the propagation channel 101 may be set to any values. Nevertheless, as illustrated in FIG. 3A, the widths of the first optical coupling regions 111b, 131b are preferably from 0.7 times to 1.3 times, more preferably from 0.8 times to 1.2 times, and even more preferably 0.9 to 1.1 times of the widths of the second optical coupling regions 101a. As the widths of the first optical coupling regions 111b, 131b become closer to those of the second optical coupling regions 101a, the equivalent refractive index of the first optical coupling regions 111b, 131b is more likely to match that of the second optical coupling regions 101a with respect to light propagating through the first optical coupling regions 111b, 131b and the second optical coupling regions 101a. This improves the efficiency of the optical coupling.

In the first embodiment, the widths of the first optical coupling regions 111b, 131b and the widths of the second optical coupling regions 101a refer to the respective widths in the portions where the respective distances between the first optical coupling regions 111b, 131b and the second optical coupling regions 101a become the smallest in the case where the widths of the first optical coupling regions 111b, 131b vary in the first optical coupling regions 111b, 131b or the widths of the second optical coupling regions 101a vary in the second optical coupling regions 101a.

In the first embodiment, the diffraction grating region 111 of the first diffraction grating portion 11 and the diffraction grating region 131 of the second diffraction grating portion 13 are both fan-shaped in the example depicted in FIGS. 2 and 3. In the first embodiment, however, the diffraction grating regions 111, 131 may have any shapes in plan view.

<Method of Manufacturing Optical Waveguide in First Embodiment>

Next, a method of manufacturing the optical waveguide 15 according to the first embodiment is described with reference to FIGS. 4 through 11. FIGS. 4 through 11 are cross-sectional views illustrating an example method of manufacturing the section illustrated in FIG. 3B.

In FIGS. 4 through 11, one diffraction grating region 111 in the first diffraction grating portion 11 is simplified and illustrated schematically to facilitate the explanation of the method of manufacturing the optical waveguide 15. FIGS. 4 through 11 are cross-sectional views, taken at a position corresponding to the A-A line in FIG. 3A, illustrating the process of manufacturing the optical waveguide 15.

Figure 4:
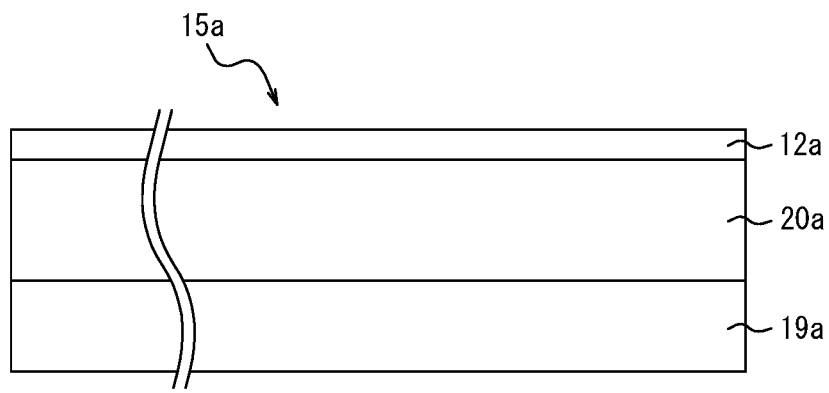
FIG. 4 is a cross-sectional view partially illustrating an optical waveguide main portion to illustrate a method of manufacturing the optical waveguide used in the optical densitometer according to the first and second embodiments of the present disclosure.

First, as illustrated in FIG. 4, a $SiO_2$ film is formed on either or both of a support substrate 19a, which is formed from silicon and ultimately serves the substrate 19, and an active substrate 12a, which is formed from silicon and from which the core layer 12 is to be formed. The support substrate 19a and the active substrate 12a are then brought into contact with each other, with the $SiO_2$ film interposed therebetween, and bonded by thermal process. The active substrate 12a is then ground, polished, or the like to a predetermined thickness to adjust the film thickness of the active substrate 12a. Consequently, an SOI substrate 15a is formed to have a "silicon-insulating layer-silicon" structure that includes the support substrate 19a, a BOX layer 20a formed on the support substrate 19a, and the active substrate 12a formed on the BOX layer 20a.

Figure 5:
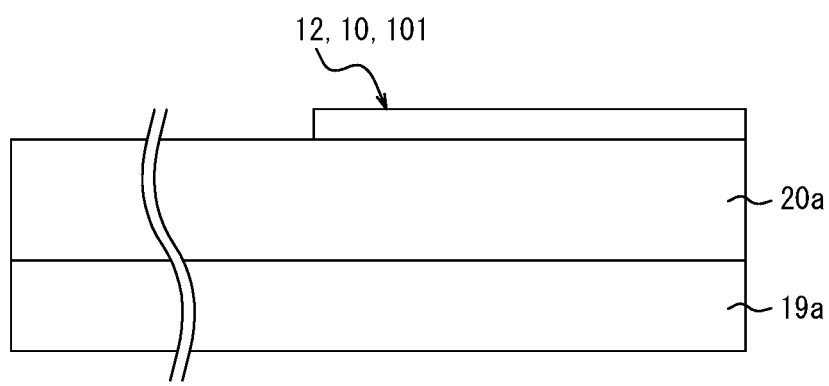
FIG. 5 is a cross-sectional view partially illustrating the optical waveguide main portion to illustrate the method of manufacturing the optical waveguide used in the optical densitometer according to the first and second embodiments of the present disclosure.

Next, the SOI substrate 15a is subjected to lithography and etching to etch the active substrate 12a to form the light propagation portion 10. The optical waveguide main portion is thus formed to include the support substrate 19a, the BOX layer 20a formed on the support substrate 19a, and the light propagation portion 10 formed on the BOX layer 20a, as illustrated in FIG. 5.

Figure 6:
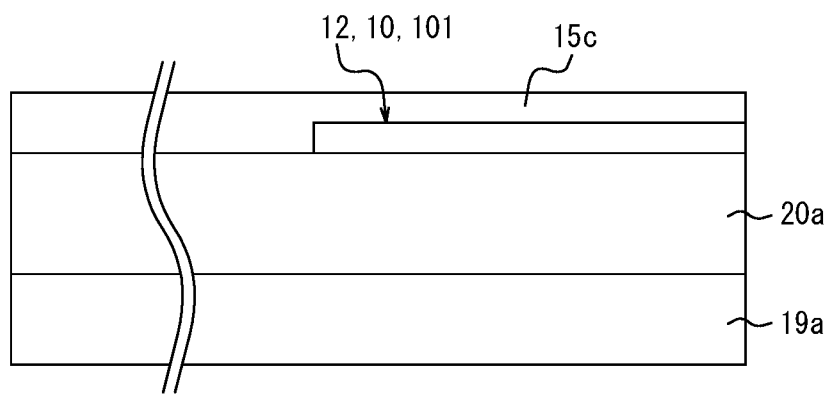
FIG. 6 is a cross-sectional view partially illustrating the optical waveguide main portion to illustrate the method of manufacturing the optical waveguide used in the optical densitometer according to the first and second embodiments of the present disclosure.

Next, as illustrated in FIG. 6, a separation film 15c for separating the subsequently formed extension region 111a of the first diffraction grating portion 11 and light propagation portion 10 is formed by depositing a $SiO_2$ film using tetraethyl orthosilicate (TEOS) as a raw material, for example. After this separation film 15c is formed on the BOX layer 20a and the light propagation portion 10, the surface is polished by chemical mechanical polishing (CMP) or the like to yield the structure illustrated in FIG. 6. The light propagation portion 10 can be separated from the first diffraction grating portion 11 in the thickness direction by the separation film 15c.

Figure 7:
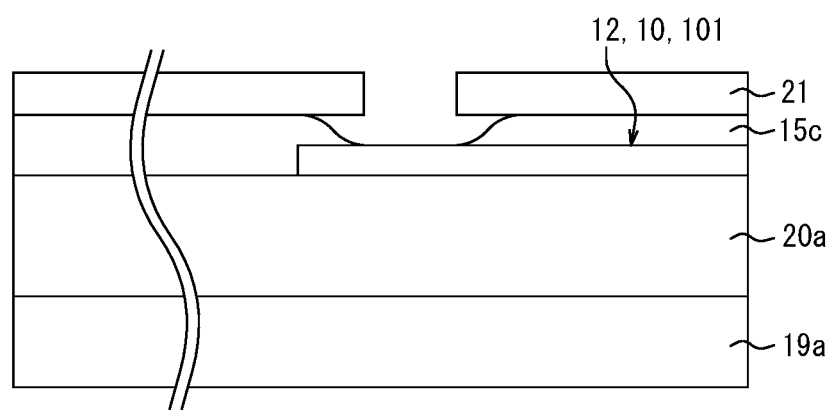
FIG. 7 is a cross-sectional view partially illustrating the optical waveguide main portion to illustrate the method of manufacturing the optical waveguide used in the optical densitometer according to the first and second embodiments of the present disclosure.

Next, as illustrated in FIG. 7, a photoresist is patterned on the separation film 15c and used as a mask layer M1 to partially etch the separation film 15c. In this step, buffered hydrofluoric acid (BHF) or the like is used for wet etching to form an inclination as gentle as possible. During the wet etching, a gentler inclination can be formed by adjusting the adhesion at the interface between the separation film 15c and the mask layer M1. In this way, a hole is defined in the separation film 15c for optically coupling the subsequently formed extension region 111a of the first diffraction grating portion 11 and the vicinity of the end of the light propagation portion 10 (propagation channel 101), as illustrated in FIG. 7.

Figure 8:
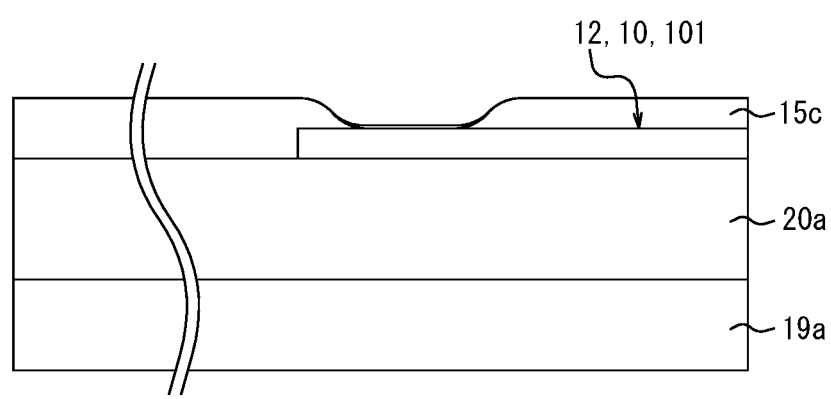
FIG. 8 is a cross-sectional view partially illustrating the optical waveguide main portion to illustrate the method of manufacturing the optical waveguide used in the optical densitometer according to the first and second embodiments of the present disclosure.

The mask layer M1 is then removed by etching, and as illustrated in FIG. 8, a $SiO_2$ film with a thickness of approximately 30 nm, for example, is formed on the exposed surface of the portion of the light propagation portion 10. This film is formed by any technique, such as oxidation or chemical vapor deposition (CVD). Furthermore, this film is not necessarily a $SiO_2$ film and may be a SiN film or the like.

Figure 9:
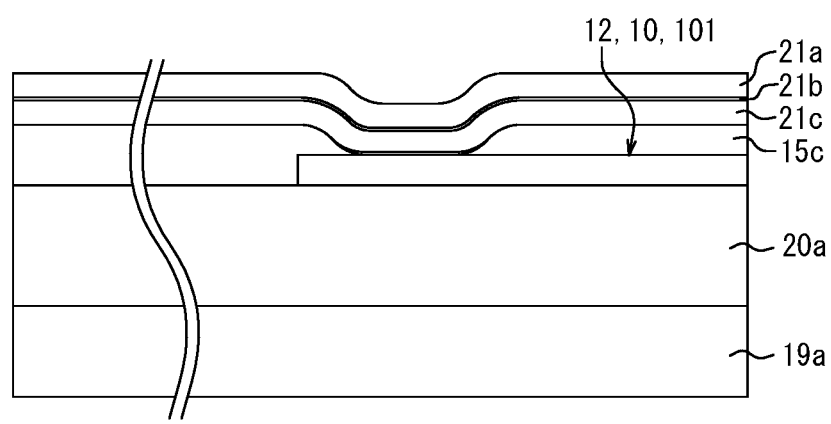
FIG. 9 is a cross-sectional view partially illustrating the optical waveguide main portion to illustrate the method of manufacturing the optical waveguide used in the optical densitometer according to the first and second embodiments of the present disclosure.

Next, as illustrated in FIG. 9, a three-layered structure of a polysilicon film (upper layer) 21a/$SiO_2$ film 21b/polysilicon film (lower layer) 21c is formed on the entire surface. The two polysilicon films 21a, 21c are, for example, formed by CVD. The $SiO_2$ film 21b that is the middle layer is formed by oxidation, CVD, or the like. The film thickness of the polysilicon film 21c that is the lower layer is preferably substantially equivalent to the film thickness of the light propagation portion 10 (propagation channel 101). In this case, the first diffraction grating portion 11 formed from the polysilicon film 21c and the light propagation portion 10 can be optically coupled to each other in a highly efficient matter. For example, the polysilicon film 21c that is the lower layer and the propagation channel 101 both preferably have a thickness of 0.6 μm.

Figure 10:
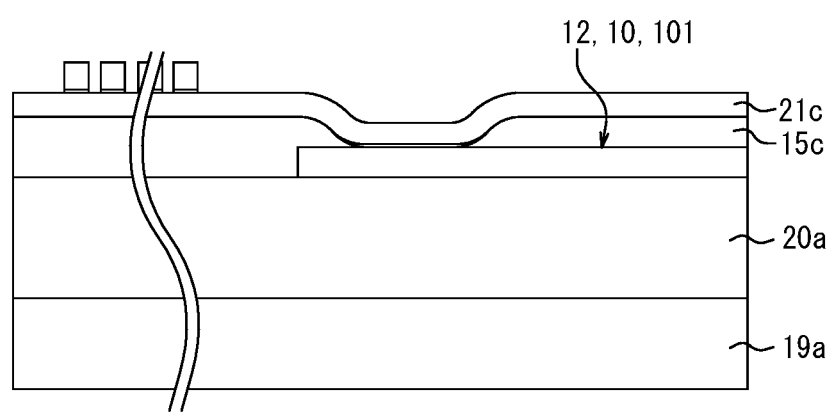
FIG. 10 is a cross-sectional view partially illustrating the optical waveguide main portion to illustrate the method of manufacturing the optical waveguide used in the optical densitometer according to the first and second embodiments of the present disclosure.

Next, as illustrated in FIG. 10, lithography and etching are used to etch the polysilicon film 21a that is the upper layer to form an uneven pattern for forming the first diffraction grating portion 11. In this step, the $SiO_2$ film 21b formed between the two polysilicon films 21a, 21c functions as a stopper film during the etching. In addition to enabling highly accurate formation of the uneven pattern, it can protect the polysilicon film 21c that is the lower layer from being excessively etched. After the uneven pattern is formed, only the exposed portions of the $SiO_2$ film 21b used as the stopper layer are removed by dry etching or wet etching.

Figure 11:
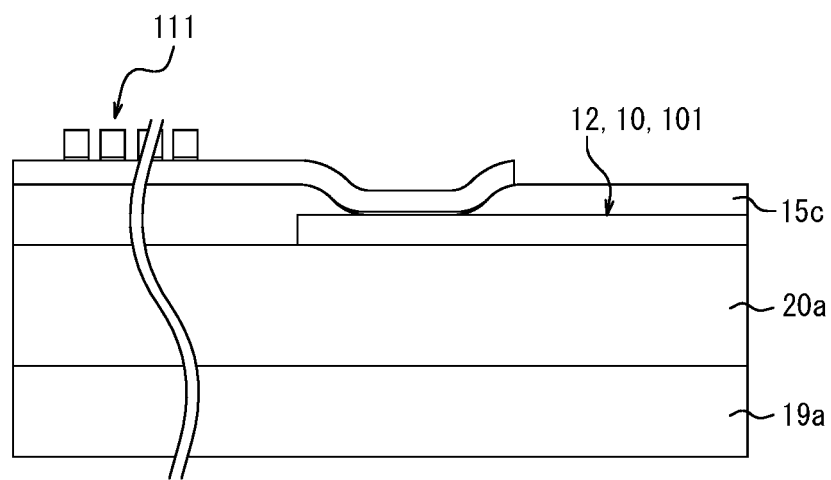
FIG. 11 is a cross-sectional view partially illustrating the optical waveguide main portion to illustrate the method of manufacturing the optical waveguide used in the optical densitometer according to the first and second embodiments of the present disclosure.

Next, as illustrated in FIG. 11, lithography and etching are used to etch the polysilicon film 21c that is the lower layer, thereby forming the profile of the first diffraction grating portion 11. Subsequently, while illustration is omitted, lithography and etching are used to remove a portion of the separation film 15c to expose the surface of a portion of the light propagation portion 10 which will serve for gas sensing. This yields an optical waveguide main portion 15b with a structure corresponding to the optical waveguide 15 of the first embodiment.

Next, the support substrate 19a is cut in a predetermined region to separate the optical waveguide main portion 15b. The optical waveguide 15 according to the first embodiment is thereby completed.

Although the above description has focused on the first diffraction grating portion 11 as the diffraction grating portion, the second diffraction grating portion 13 can be formed in the similar manner.

Second Embodiment

An optical waveguide according to a second embodiment of the present disclosure is described with reference to FIGS. 1 through 3, similarly to the first embodiment. Elements that are not described below are similar to the corresponding elements in the first embodiment, and a description of the elements common to the first embodiment is omitted.

A sensor employing the ATR technique can improve the sensitivity of the sensor by expanding the region of interaction between an evanescent wave EW extending from a core layer and a substance of interest (i.e. by expanding the exposed portion of the core layer). In addition, in the sensor employing the ATR technique, it is also desirable to cause more evanescent waves that have been introduced to the core layer to extend, for the purpose of improving the sensitivity of a sensor. In the case where a substrate of an optical waveguide, however, is in immediate proximity to the light propagation portion, an evanescent wave extending from the light propagation portion may reach the substrate, and a part of light propagating through the light propagation portion may leak to the substrate. In order to suppress leakage of evanescent waves to the substrate to thereby improve the propagation efficiency, it is thus important to control the distance L2 between the light propagation portion and the substrate to a certain value.

Figure 15A:
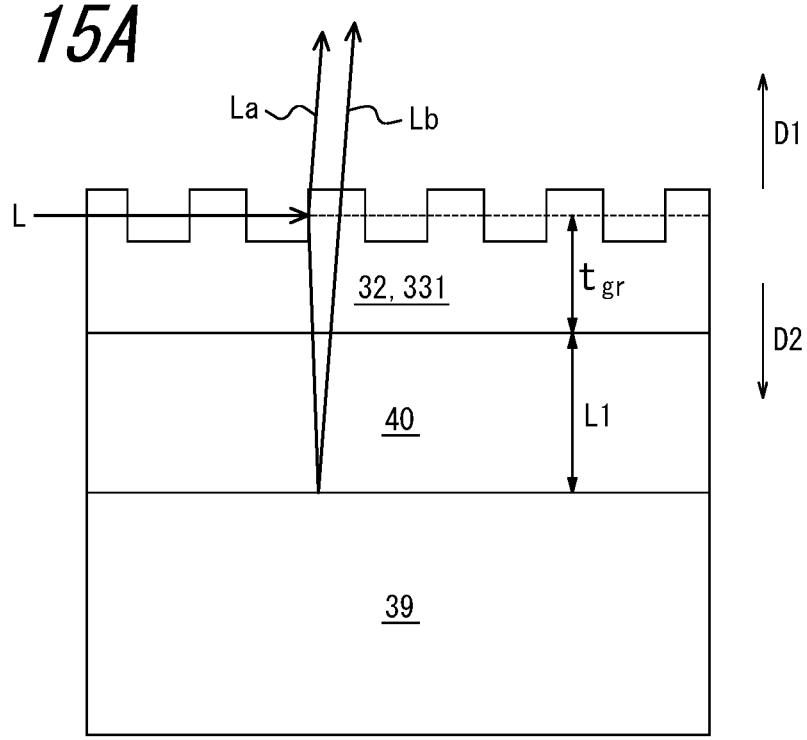
FIGS. 15A and 15B are diagrams for illustrating interference of light that may occur in a diffraction grating region.

In addition, in the diffraction grating region for extracting light from the core layer or for introducing light into the core layer, the extraction efficiency and the introducing efficiency (i.e., diffraction efficiency) deviate due to interference of light, as illustrated in FIG. 15. A description will be made with reference to an example where light is extracted from the core layer. As illustrated in FIG. 15A, when light propagating through the core layer is diffracted toward the external side D1 (the surface side in the thickness direction), diffracted light has light component La that is bent from a diffraction grating region 331 (corresponding to the diffraction grating region 131 of the second diffraction grating portion 13 of the present application) to the external side D1, as well as light component Lb that is bent toward the substrate side D2 in the thickness direction of the optical waveguide. The light component Lb bent by the diffraction grating region formed on the surface of a core layer 32 toward the substrate side D2 in the thickness direction passes through the core layer 32 and the support layer 40, and reaches the boundary with (surface of) the substrate 39. The light may be reflected at the boundary back to the diffraction grating region 331. As a result, the light component Lb reflected back to the diffraction grating region 331 may interfere with the light component La extracted from the diffraction grating region 331 to the outside without being reflected, in the diffraction grating region 331. The light component Lb takes a round trip through the core layer 32 and the support layer 40 and the phase of light component Lb delays behind the light component La. When the delayed phase is an integral multiple of $2\pi$, constructive interference between the light component La and the light component Lb is maximized. Here, the effective film thickness $t_{gr}$ of the core layer 32 is assumed to be a sum of the film thickness of the core layer 32 in recessed portions of the diffraction grating region 331, and a half the film thickness difference of the core layer 32 between recessed portions and protruding portions of the diffraction grating region 331. The phase delay due to one round trip of the core layer 32 is expressed by the following Expression (8), and the phase delay due to one round trip of the support layer 40 having a film thickness L1 is expressed by the following Expression (9):

$$2\pi \frac{2 n_{gr} t_{gr}}{\lambda_0} \quad \text{Expression (8)}$$

$$2\pi \frac{2 n_{L1} L1}{\lambda_0} \quad \text{Expression (9)}$$

where $n_{gr}$ and $n_{L1}$ represent the respective refractive indices of materials forming the core layer 32 and the support layer 40, and $\lambda_0$ represents the wavelength, in vacuum, of light propagating through the core layer 32. Further, when the light is reflected at the boundary between the support layer 40 and the substrate 39, the phase further shifts by 7C if the refractive index of the support layer 40 is smaller than the refractive index of the substrate 39. In view of these, the light component La interferes constructively with the light component Lb when the condition of the following Expression (10) is met:

$$2\pi m = 2\pi \frac{2 n_{gr} t_{gr}}{\lambda_0} + 2\pi \frac{2 n_{L1} L1}{\lambda_0} + \pi \quad \text{Expression (10)}$$

where m is a natural number. Thus, in order to efficiently extract light from the diffraction grating region 331 to the external side D1, it is important to control the phase difference between the reflected light component Lb and the non-reflected light component La, in other words, to control the distance L1 between the diffraction grating region 331 and the substrate 39 to a certain value, as in controlling the distance L2 between the light propagation portion and the substrate.

Figure 15B:
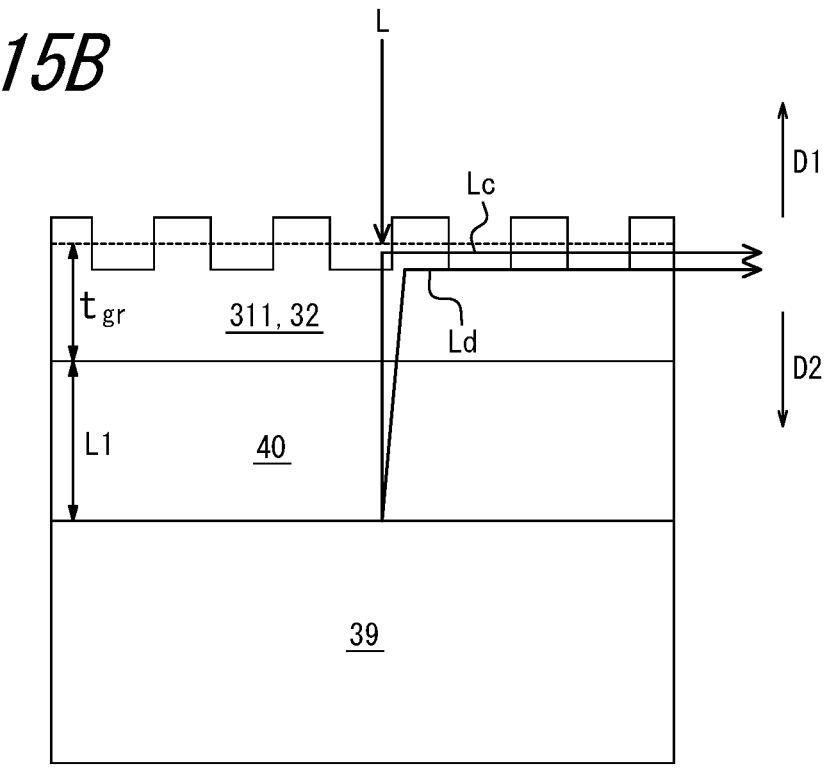

The above-mentioned principle is similarly applicable for introducing light from a light source into the core layer. Although a detailed description is omitted, in the diffraction grating region for introducing light into the core layer, as illustrated in FIG. 15B, when light enters a diffraction grating region 311 from the external side D1 and is introduced into the core layer, the introduced light has light component Lc introduced into the core layer from the diffraction grating region 311 (corresponding to the diffraction grating region 111 of the first diffraction grating portion 11 of the present application), as well as light component Ld passing through the diffraction grating region 311 and travels toward the substrate side D2 in the thickness direction. The light component Ld traveling toward the substrate side D2 in the thickness direction passes through the core layer 32 and the support layer 40. The light then reaches the boundary with (surface of) the substrate 39, and may be reflected at the boundary back to the diffraction grating region 311. As a result, the light component Ld reflected back to the diffraction grating region 311 may interfere with the light component Lc directly introduced into the core layer from the external side D1, in the diffraction grating region 311. The phenomenon similar to the light extraction occurs. Thus, in order to efficiently introduce light into the core layer from the diffraction grating region 311, it is important to control the phase difference between the reflected light component Ld and the non-reflected light component Lc, i.e., to control the distance L1 between the diffraction grating region 331 and the substrate 39 to a certain value, as in controlling the distance L2 between the light propagation portion and the substrate.

Accordingly, in such a sensor, it is required to optimize the distances L1 and L2 in the optical waveguide by taking into consideration the diffraction efficiency of the diffraction grating region for extracting light from the core layer or introducing light into the core layer, and the propagation efficiency of the light propagation portion.

In a conventional optical waveguide, however, because a light propagation portion and a diffraction grating region are formed on a flat support layer on an SOI substrate or the like, the distance between the light propagation portion and the substrate equals the distance between the diffraction grating region and the substrate. It is thus difficult to design the optical waveguide so as to improve both the diffraction efficiency of the diffraction grating region and the propagation efficiency of the light propagation portion.

To meet the needs, in an optical waveguide 15 of the second embodiment, as illustrated in FIG. 3, a substrate 19 and a core layer 12 are separated from each other, and the distance L1 between diffraction grating region 111 or 131 of the first diffraction grating portion 11 or the second diffraction grating portion 13 and the substrate 19 differs from the distance L2 between the light propagation portion 10 and the substrate 19 (illustration of the diffraction grating region 131 of the second diffraction grating portion 13 is omitted). This enables the distance L1 between the diffraction grating regions 111 or 131 of the first diffraction grating portion 11 or the second diffraction grating portion 13 and the substrate 19 and the distance L2 between the light propagation portion 10 and the substrate 19 to be controlled independently from each other. This makes it possible to improve both the diffraction efficiencies of the first diffraction grating portion 11 and the second diffraction grating portion 13 and the propagation efficiency of the light propagation portion 10.

Here, in the optical waveguide 15 of the second embodiment, the method to separate the substrate 19 and the core layer 12 from each other to control the distance L1 and the distance L2 so as to differ from each other is not particularly limited. In the illustrated embodiment, as described above, the substrate 19 and the core layer 12 are separated by providing the support layer 20 between the substrate 19 and the core layer 12. Further, as illustrated in FIG. 3, the distance L1 and the distance L2 are controlled so as to differ from each other by disposing the first diffraction grating portion 11 or the second diffraction grating portion 13 and the light propagation portion 10 in the different layers. More specifically, the first diffraction grating portion 11 or the second diffraction grating portion 13 and the light propagation portion 10 are spatially separated in the thickness direction so that the first diffraction grating portion 11 or the second diffraction grating portion 13 and the light propagation portion 10 are disposed in the different layers (in this case, the first diffraction grating portion 11 or the second diffraction grating portion 13 and the light propagation portion 10 may be formed from the same or different materials). Controls of the distance L1 and the distance L2 become easier when the first diffraction grating portion 11 or the second diffraction grating portion 13 and the light propagation portion 10 are formed from different materials. Note that the first diffraction grating portion 11 or the second diffraction grating portion 13 and the light propagation portion 10 may not be necessarily separated (in other words, the first diffraction grating portion 11 or the second diffraction grating portion 13 and the light propagation portion 10 may be in at least partial contact with each other).

In the second embodiment, the material forming a separation portion between the substrate and the diffraction grating region preferably has a refractive index smaller than the refractive index of the substrate, and the distance L1 between the diffraction grating region 111 or 131 of the first diffraction grating portion 11 or the second diffraction grating portion 13 and the substrate 19 satisfies preferably the following Expression (11), more preferably the following Expression (12), and even more preferably the following Expression (13):

$$\frac{(2m-1)\lambda_0 - 4n_{gr}t_{gr}}{4n_{L1}} - \frac{3\lambda_0}{16n_{L1}} \leq \quad \text{Expression (11)}$$
$$L1 \leq \frac{(2m-1)\lambda_0 - 4n_{gr}t_{gr}}{4n_{L1}} + \frac{3\lambda_0}{16n_{L1}};$$

$$\frac{(2m-1)\lambda_0 - 4n_{gr}t_{gr}}{4n_{L1}} - \frac{\lambda_0}{8n_{L1}} \leq \quad \text{Expression (12)}$$
$$L1 \leq \frac{(2m-1)\lambda_0 - 4n_{gr}t_{gr}}{4n_{L1}} + \frac{\lambda_0}{8n_{L1}}; \text{ and}$$

-continued $$\frac{(2m-1)\lambda_0 - 4n_{gr}t_{gr}}{4n_{L1}} - \frac{\lambda_0}{16n_{L1}} \leq \quad \text{Expression (13)}$$
$$L1 \leq \frac{(2m-1)\lambda_0 - 4n_{gr}t_{gr}}{4n_{L1}} + \frac{\lambda_0}{16n_{L1}},$$

where $\lambda_0$ represents the average wavelength, in vacuum, of light propagating through the core layer 12, $n_{L1}$ represents the refractive index of the material present between the substrate 19 and the diffraction grating region 111 or 131 of the first diffraction grating portion 11 or the second diffraction grating portion 13, $t_{gr}$ represents the effective film thickness of the diffraction grating region 111 or 131 of the first diffraction grating portion 11 or the second diffraction grating portion 13, $n_{gr}$ represents the refractive index of the material forming the diffraction grating region 111 or 131 of the first diffraction grating portion 11 or the second diffraction grating portion 13, and m is a natural number. In the case where a plurality of materials are present between the substrate 19 and the diffraction grating region 111 or 131 of the first diffraction grating portion 11 or the second diffraction grating portion 13, the effective value calculated as $\{\Sigma(n_{L1i}^2 \times A_{L1i})\}^{1/2}$ is used as $n_{L1}$, where $n_{L1i}$ represents the refractive index of each material present between the substrate 19 and the diffraction grating region 111 or 131 of the first diffraction grating portion 11 or the second diffraction grating portion 13, and $A_{L1i}$ represents the occupation ratio of the each material between the diffraction grating region 111 or 131 of the first diffraction grating portion 11 or the second diffraction grating portion 13 and the substrate 19 (the occupation ratio in the thickness direction in the second embodiment). The effective film thickness of the diffraction grating region 111 or 131 in the first diffraction grating portion 11 or the second diffraction grating portion 13 is defined as a sum of the film thickness of the core layer 12 in recessed portions of the diffraction grating region 111 or 131, and a half the film thickness difference of the core layer 12 between recessed portions and protruding portions of the diffraction grating region 111 or 131. Further, in the case in which a plurality of materials are present for forming the diffraction grating region 111 or 131 of the first diffraction grating portion 11 or the second diffraction grating portion 13, the effective value calculated as $\{\Sigma(n_{gri}^2 \times A_{gri})\}^{1/2}$ is used as $n_{gr}$, where $n_{gri}$ represents the refractive index of each material forming the core region 12 in recessed portions of the diffraction grating region 111 or 131, and $A_{gri}$ represents the occupation ratio of the each material in the recessed portions of the diffraction grating region 111 or 131, in the core layer 12 in the recessed portions of the diffraction grating region 111 or 131. When the distance L1 satisfies one of the above expressions, the diffraction efficiency of light at the first diffraction grating portion 11 or the second diffraction grating portion 13 is maintained to a high level.

In the second embodiment, the distance L1 can be controlled so as to satisfy one of the above expressions by adjusting the thickness of the support layer 20, and the thickness of an intermediate layer 22 between the diffraction grating region 111 or 131 of the first diffraction grating portion 11 or the second diffraction grating portion 13 and the light propagation portion 10. Note that the intermediate layer 22 may be a layer made from a material (including the air) having a relatively lower refractive index than that of the core layer 12, and is a silicone oxide ($SiO_2$) film in the illustrated example. When the intermediate layer 22 and the support layer 20 are formed as silicon oxide films, the refractive index of the material between the diffraction grating region 111 or 131 of the first grating portion 11 or the second grating portion 13 and the substrate 19 is estimated to be about 1.4. Further, the average wavelength $\lambda_0$, in vacuum, of light propagating through the core layer 12 is about 4.3 μm, for example.

Further, in the second embodiment, the distance L2 at which the light propagation portion 10 and the substrate 19 are separated from each other is equal to or greater than the distance given by the following Expression (14):

$$\frac{6\lambda_0}{2\pi\sqrt{n_{pro}^2 - n_{L2}^2}} \quad \text{Expression (14)}$$

where $\lambda_0$ represents the average wavelength, in vacuum, of light propagating through the core layer 12, $n_{pro}$ represents the refractive index of the material forming the light propagation portion 10, and $n_{L2}$ represents the refractive index of the material present in the portion sandwiched between the light propagation portion 10 and the substrate 19. In the case where a plurality of materials are present in the portion sandwiched between the light propagation portion 10 and the substrate 19, the largest refractive index among the refractive indices of the plurality of materials is used as $n_{L2}$. By setting the distance L2 to the predetermined distance, leakage of an evanescent wave EW extending from the light propagation portion 10 to the substrate 19 is suppressed to a sufficiently low level, thereby further improving the propagation efficiency of the light propagation portion 10.

In the second embodiment, the distance L2 can be controlled to the aforementioned predetermined distance by using an SOI substrate having a support layer 20 of which thickness is controlled.

In the second embodiment, the distance L1 and the distance L2 can have any relationship. For example, in an optical densitometer for detecting $CO_2$, which is a gas typically present in the environment, infrared radiation with a wavelength of about 4.3 μm (wavelength in vacuum) is typically used as the light to propagate through the core layer 12. When the separation portion between the diffraction grating region 111 or 131 of the first diffraction grating portion 11 or the second diffraction grating portion 13 and the substrate 19 is formed as a silicon oxide film and the diffraction grating region 111 or 131 is formed from silicon with an effective film thickness of about 0.9 μm, the parameters giving the distance L1 are: $\lambda_0$=4.3 μm, $n_{L1}$=1.4, $n_{gr}$=3.4, and $t_{gr}$=about 0.9 μm. The distance L1 is preferably from 4.1 μm to 5.3 μm, more preferably from 4.3 μm to 5.1 μm, and even more preferably from 4.5 μm to 4.9 μm, for example. Under these conditions, the distance L2 is about 2.5 μm, for example. In the case where a portion serving as the distance L2 is formed by using a buried oxide film (BOX) layer on a bonded-type SOI substrate, the process throughput decreases, resulting in a cost increase, as the BOX layer becomes thicker. It is thus desirable to optimize the distance L1 while maintaining the distance L2 to a value of about 2.5 μm in view of both the optical performances and the cost.

Further, in the optical waveguide 15 of the second embodiment, the entire diffraction grating portions 11 and 13, including the extension regions 111a, 131a, are separated from the light propagation portion 10 in the thickness direction, and the distance L1 between the diffraction grating region 111, 131 and the substrate 19 differs from the distance L2 between the light propagation portion 10 and the substrate 19 by a difference equal to or greater than the film thickness of the light propagation portion 10 throughout the diffraction grating regions 111, 131.

<Method of Manufacturing Optical Waveguide in Second Embodiment>

The method of manufacturing the optical waveguide 15 according to the second embodiment is the same as the manufacturing method described in the first embodiment, and a detailed description thereof is omitted.

Third Embodiment

Next, an optical waveguide according to a third embodiment of the present disclosure is now described with reference to FIGS. 12 and 13. Elements that are the same as those of the first embodiment are denoted by the same reference signs, and a description thereof is omitted.

Figure 12:
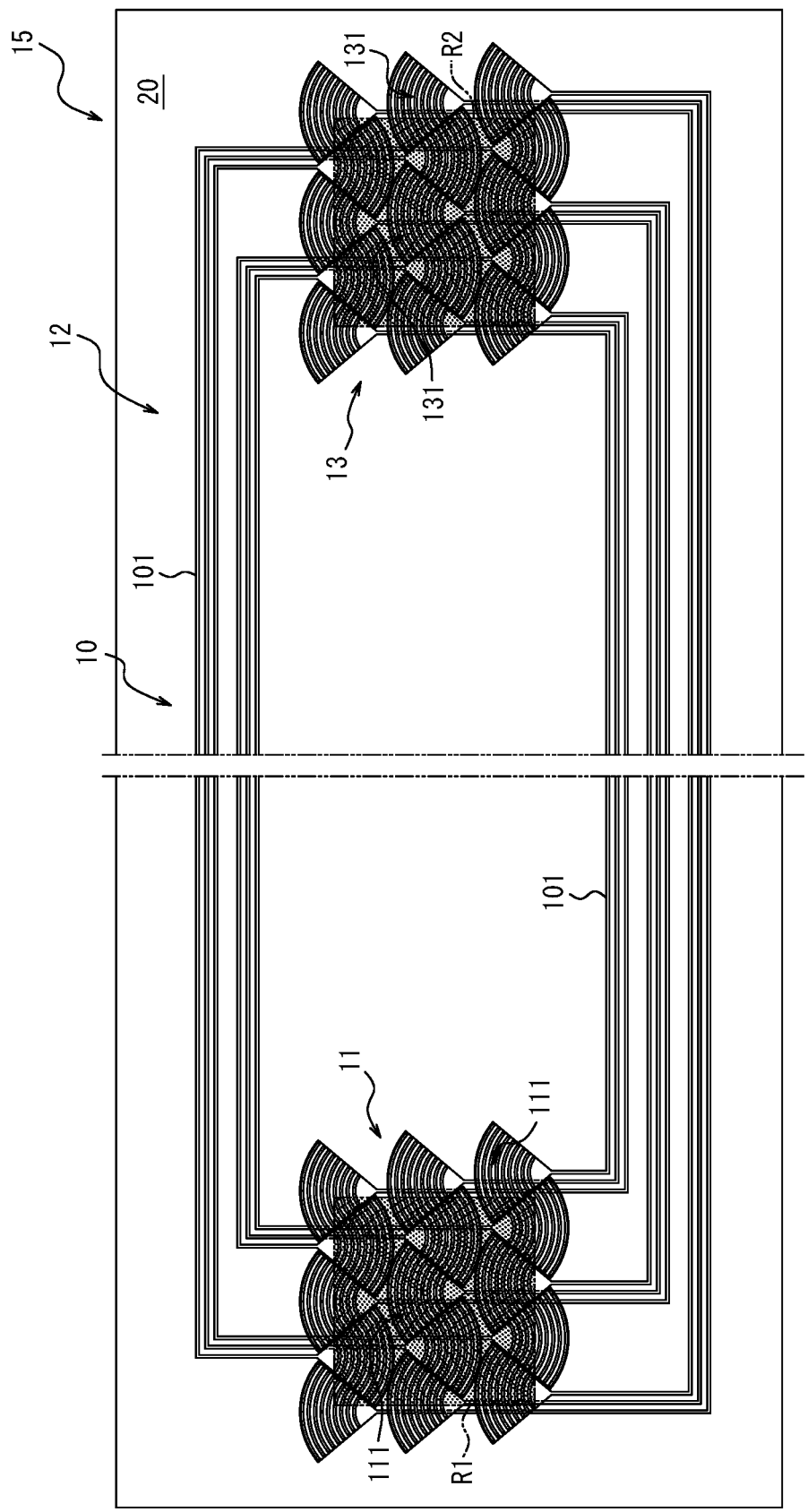
FIG. 12 is a schematic plan view illustrating an optical waveguide used in an optical densitometer according to a third embodiment of the present disclosure from a light source side or a photodetector side.

In the third embodiment, as illustrated in FIG. 12, a first diffraction grating portion 11 has a plurality of diffraction grating regions 111. At least two diffraction grating regions 111 among the plurality of the diffraction grating regions 111 in the first diffraction grating portion 11 receive light emitted from the same light-emitting surface of a light source 17. Specifically, the range R1 in FIG. 12 is a range, in plan view, yielded by projecting the range considered to be the same light-emitting surface within the light-emitting surface of the light source 17 onto the diffraction grating portion 11 in a direction orthogonal to the light-emitting surface. At least two diffraction grating regions 111 are present within this range R1.

There has been a problem in that light cannot be introduced into an optical waveguide (core layer 12) from a light-emitting element with high efficiency when light is received from the light-emitting element on one large diffraction grating region. In contrast, as illustrated in FIG. 12, in the configuration where light emitted from the same light-emitting surface of the light source 17 is received on at least two first diffraction grating regions 111 among the plurality of diffraction grating regions 111, the diffraction grating regions 111 can be made relatively smaller. A reduced efficiency due to a large diffraction grating region can be suppressed. Light from the light-emitting element can therefore be introduced into the optical waveguide with high efficiency.

Note that the range considered to be the same light-emitting surface is not necessarily limited to one light-emitting surface. In the case of a plurality of light-emitting surfaces, the total range of the plurality of light-emitting surfaces is considered one light-emitting surface when the light outputted from each light-emitting surface is synchronously controlled by a common drive system.

All of the diffraction grating regions 111 of the first diffraction grating portion 11 are located within the range R1 in the example in FIG. 12, but a diffraction grating region 111 may be located outside of the range R1. Even if a diffraction grating region 111 is located outside of the range R1, or if a part of the diffraction grating region 111 is outside the range R1, light can be introduced into the core layer 12 by the diffraction grating region 111 located outside, or the part located outside, since light spreads from the light-emitting surface of the light source 17.

Figure 13A:
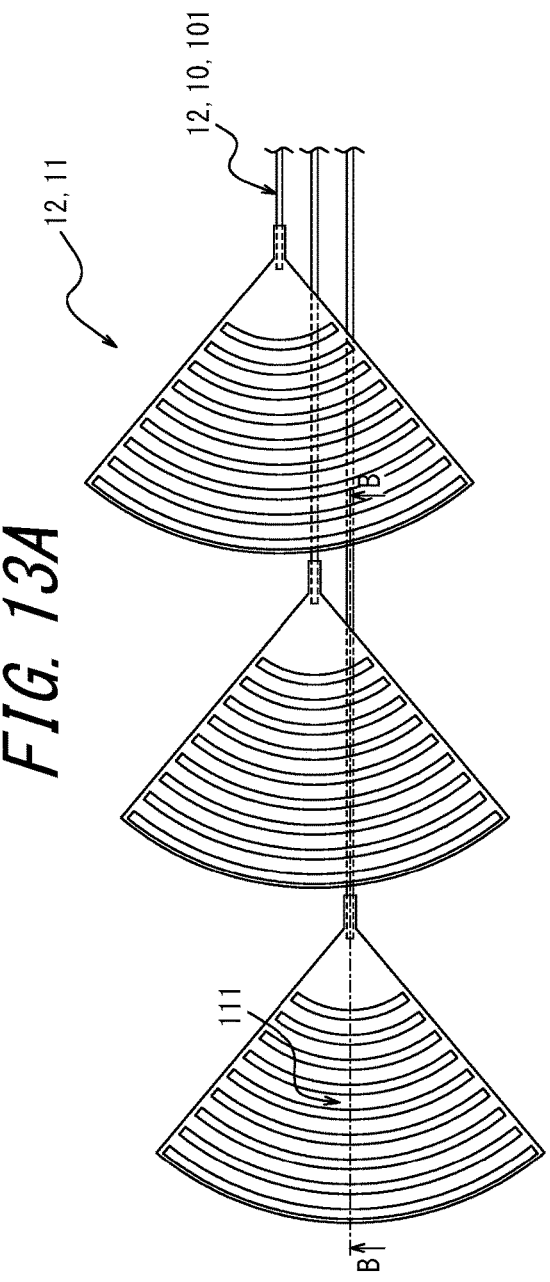
FIG. 13A is a schematic plan view illustrating a part of a first diffraction grating portion and a propagation channel of the optical waveguide in FIG. 12.
Figure 13B:
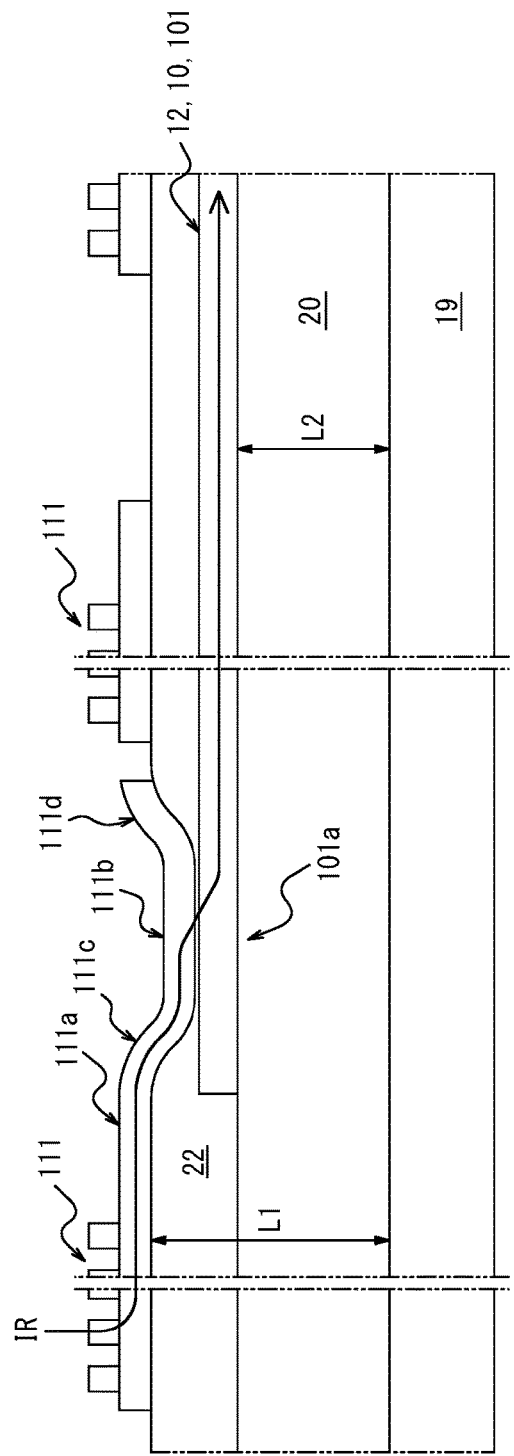
FIG. 13B is a cross-sectional view illustrating a cross section along the line B-B.
Figure 14:
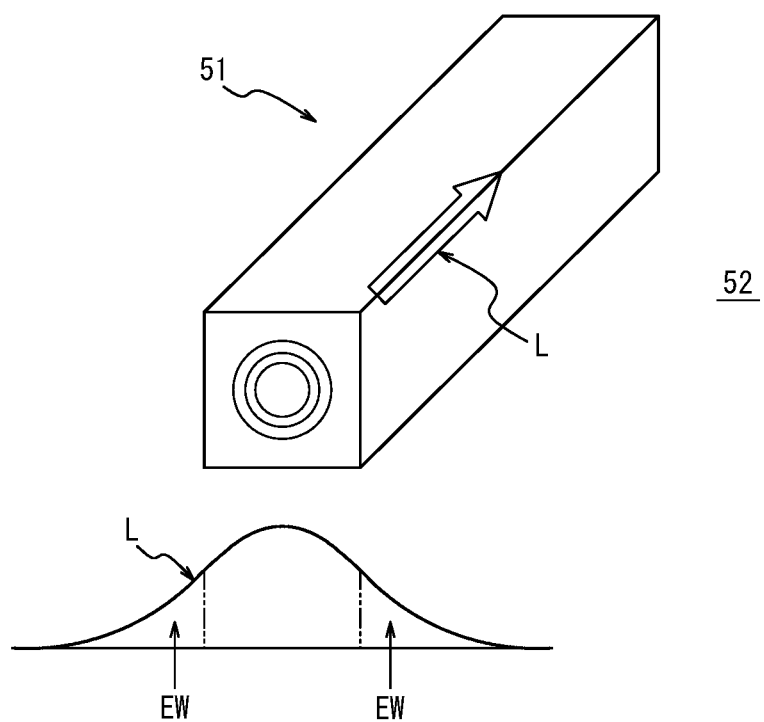
FIG. 14 illustrates an evanescent wave of light propagating through an optical waveguide.

In the third embodiment, as illustrated in FIG. 13, each diffraction grating region 111 of the first diffraction grating portion 11 has an extension region 111a, and each diffraction grating region 111 and the extension region 111a connected to the diffraction grating region 111 are all made from materials different from each propagating path 101. Each extension region 111a and the corresponding propagation channel 101 are separated from each other in the thickness direction. As a result, as illustrated, on the surface side in the thickness direction of one diffraction grating region 111 relative to one propagation channel 101 optically coupled to an extension region 111a connected to the one diffraction grating region 111, another diffraction grating region 111 can be formed so as to be separated from the one propagation channel 101. By forming the another diffraction grating region 111 on the surface side in the thickness direction relative to the one propagation channel 101, diffraction grating regions 111 can be disposed more densely in the first diffraction grating portion 11, which enables light from the light-emitting element to be introduced into the optical waveguide with high efficiency.

In the example in FIG. 12, all of the propagation channels 101 of the light propagation portion 10 are present on the substrate side in the thickness direction relative to the diffraction grating regions 111 of the first diffraction grating portion 11, and the second optical coupling regions 101a of all of the propagation channels 101 are optically coupled to the corresponding first optical coupling regions 111b of extension regions 111a connecting to the diffraction grating regions 111. Similarly to the first diffraction grating portion 11, in the diffraction grating region 131 of the second diffraction grating portion 13, all of the propagation channels 101 are optically coupled to the corresponding diffraction grating regions 131 via the first optical coupling regions 131b and the second optical coupling regions 101a.

In the third embodiment, although the diffraction grating portion includes the plurality of diffraction grating regions, a part of the diffraction grating regions may be connected to the corresponding extension regions so that the first optical coupling regions of the extension regions and the second optical coupling regions 101a of the propagation channels 101 are optically coupled to each other, and the remaining diffraction grating region may be directly connected to the propagation channels 101 bypassing the first optical coupling regions and the second optical coupling regions 101a of the propagation channels 101.

In the optical waveguide 15 of the third embodiment, the light propagation portion 10 of the optical waveguide 15 has a plurality of propagation channels 101 that each receive the light received by one diffraction grating region 111, propagate the light, and guide the light to one diffraction grating 131, as illustrated in FIG. 12. This enables the diffraction grating regions 111 in the first diffraction grating portion 11 and the diffraction grating regions 131 in the second diffraction grating portion 13 to be disposed more densely, which achieves more efficient utilization of light from the light-emitting element.

In the illustrated example, all of the plurality of propagation channels 101 are arranged in parallel between the diffraction grating regions 111 and the diffraction grating regions 131. The plurality of propagation channels 101, however, are not necessarily arranged in parallel in the third embodiment, and the propagation channels 101 may take any forms. For example, propagation channels 101 may be merged or may be branched between the diffraction grating regions 111 and the diffraction grating regions 131.

In the third embodiment, the diffraction grating regions 111 in the first diffraction grating portion 11 are all in the same size and shape, but the diffraction grating regions 111 may have different sizes and shapes as the first diffraction grating portion 11. The optical waveguide 15 can be provided with multifunctionality by forming diffraction grating regions with different sizes and shapes. An example of multifunctionality is to vary the period of unevenness forming each diffraction grating region 111 to enable selection of many wavelengths.

The at least two diffraction grating regions 111 among the plurality of diffraction grating regions 111 in the third embodiment are preferably located in a 5×5 mm$^2$ range, more preferably a 1×1 mm$^2$ range, and even more preferably a 500×500 μm$^2$ range. This enables the light-emitting element and the optical waveguide 15 to be coupled highly efficiently.

Further, in the third embodiment, the ratio of the area of diffraction grating regions 111 is preferably 30% or more and more preferably 60% or more in the 5×5 mm$^2$ range or the 1×1 mm$^2$ range or the 500×500 μm$^2$ range. This enables the light-emitting element and the optical waveguide 15 to be coupled highly efficiently.

In the third embodiment, the second diffraction grating portion 13 may have any structure. Specifically, the structure of the second diffraction grating portion 13 in the illustrated example is the same as the structure of the first diffraction grating portion 11 but may instead be different. A range R2 in FIG. 12 is a range, in plan view of the substrate 19 of the optical waveguide 15 (when looking towards the substrate 19), yielded by projecting the range of the detector onto the second diffraction grating portion 13 in a direction orthogonal to the detection surface of the detector arranged. The size and arrangement of the diffraction grating regions 131 in the second diffraction grating portion 13 may be changed in any way depending on the detector, for example.

<Method of Manufacturing Optical Waveguide in Third Embodiment>

The method of manufacturing the optical waveguide 15 according to the third embodiment is the same as the manufacturing method described in the first embodiment except for change of the pattern used in lithography, and a detailed description thereof is omitted.

INDUSTRIAL APPLICABILITY

The present disclosure can provide an optical densitometer and an optical waveguide provided with a diffraction grating portion and a light propagation portion both exhibiting high performances as a core layer more easily.

The invention claimed is:

1. An optical densitometer for measuring a density of a gas or liquid of interest, the optical densitometer comprising:
   a light source capable of introducing light into a core layer;
   a detector capable of receiving the light that has propagated through the core layer; and
   an optical waveguide, the optical waveguide comprising:
      a substrate; and
      the core layer comprising a light propagation portion capable of propagating the light in an extending direction of the light propagation portion, and a diffraction grating portion,
   the diffraction grating portion comprising a diffraction grating region and an extension region connected to the diffraction grating region, and
   a first optical coupling region included in the extension region and a second optical coupling region included in the light propagation portion being optically coupled with respect to the light propagating through the core layer, wherein
   at least a portion of the diffraction grating portion is spatially separated from the light propagation portion via a material having a relatively lower refractive index than that of the core layer in a thickness direction, and in a region where the light propagation portion and the diffraction grating portion overlap in plan view, a first distance modification region is provided in which a distance in a thickness direction between the diffraction grating portion and the light propagation portion reduces in a direction approaching from the diffraction grating region toward the first optical coupling region.

2. The optical densitometer according to claim 1, wherein the extension region and the light propagation portion are separated from each other in a thickness direction.

3. The optical densitometer according to claim 1, wherein a propagation direction of the light propagating through the core layer does not substantially change before and after a transition from the first optical coupling region to the second optical coupling region, and/or before and after a transition from the second optical coupling region to the first optical coupling region.

4. The optical densitometer according to claim 1, wherein the first optical coupling region has an equivalent refractive index from 0.7 times to 1.3 times of an equivalent refractive index of the second optical coupling region with respect to the light propagating through the core layer.

5. The optical densitometer according to claim 1, wherein the first optical coupling region has a film thickness from 0.7 times to 1.3 times of a film thickness of the second optical coupling region.

6. The optical densitometer according to claim 1, wherein a refractive index of a material forming the first optical coupling region is from 0.9 times to 1.1 times of a refractive index of a material forming the second optical coupling region.

7. The optical densitometer according to claim 1, wherein a distance between the first optical coupling region and the second optical coupling region is equal to or smaller than a distance given by the following Expression (1):

$$\frac{3\lambda_0}{2\pi\sqrt{n_{coup}^2 - n_{mid}^2}} \quad \text{Expression (1)}$$

where $\lambda_0$ represents an average wavelength, in vacuum, of the light propagating through the core layer, $n_{coup}$ represents a refractive index of the material forming the first optical coupling region or the second optical coupling region, and $n_{mid}$ represents a refractive index of a material present in a portion sandwiched between the first optical coupling region and the second optical coupling region.

8. The optical densitometer according to claim 1, wherein the distance between the first optical coupling region and the second optical coupling region is 0.7 μm or smaller.

9. The optical densitometer according to claim 1, wherein at least one of the light propagation portion and the extension region comprises an end portion, the end portion of the light propagation portion and the diffraction grating portion are separated from each other, and/or the end portion of the extension region and the light propagation portion are separated from each other, at a distance greater than a distance given by the following Expression (2):

$$\frac{3\lambda_0}{2\pi\sqrt{n_{pro}^2 - n_{gap}^2}} \quad \text{Expression (2)}$$

where $\lambda_0$ represents the average wavelength, in vacuum, of the light propagating through the core layer, $n_{pro}$ represents a refractive index of a material forming the light propagation portion or the extension region, and $n_{gap}$ represents a refractive index of a material present in a portion sandwiched between the end portion of the light propagation portion and the diffraction grating portion, or a refractive index of a material present in a portion sandwiched between the end portion of the extension region and the light propagation portion.

10. The optical densitometer according to claim 1, wherein in the first distance modification region, the distance from the light propagation portion gradually changes from a distance greater than a distance given by the following Expression (3) to a distance equal to or smaller than a distance given by the following Expression (4):

$$\frac{3\lambda_0}{2\pi\sqrt{n_{pro}^2 - n_{gap}^2}} \quad \text{Expression (3)}$$

where $\lambda_0$ represents the average wavelength, in vacuum, of the light propagating through the core layer, $n_{pro}$ represents the refractive index of the material forming the light propagation portion or the extension region, and $n_{gap}$ represents a refractive index of a material present in a portion sandwiched between the light propagation portion and the at least a portion of the diffraction grating portion, and $$\frac{3\lambda_0}{2\pi\sqrt{n_{coup}^2 - n_{mid}^2}} \quad \text{Expression (4)}$$

where $\lambda_0$ represents the average wavelength, in vacuum, of the light propagating through the core layer, $n_{coup}$ represents the refractive index of the material forming the first optical coupling region or the second optical coupling region, and $n_{mid}$ represents the refractive index of the material present in the portion sandwiched between the first optical coupling region and the second optical coupling region.

11. The optical densitometer according to claim 1, wherein a maximum angle of the first distance modification region relative to the light propagation portion is 45° or less.

12. The optical densitometer according to claim 1, wherein in the region where the diffraction grating portion and the light propagation portion overlap in plan view, a second distance modification region is provided in which the distance between the diffraction grating portion and the light propagation portion increases in a direction away from the first optical coupling region toward the diffraction grating region.

13. The optical densitometer according to claim 1, wherein at least a portion of the diffraction grating portion is made from a material different from a material of the light propagation portion.

14. The optical densitometer according to claim 13, wherein the material forming the light propagation portion is monocrystalline silicon, and the material forming the diffraction grating portion comprises polycrystalline silicon or amorphous silicon.

15. The optical densitometer according to claim 1, wherein the substrate and the core layer are disposed so as to be separated from each other, and a distance L1 between the diffraction grating region and the substrate differs from a distance L2 between the light propagation portion and the substrate.

16. The optical densitometer according to claim 15, wherein the distance L2 at which the light propagation portion and the substrate are separated from each other is equal to or greater than a distance given by the following Expression (5):

$$\frac{6\lambda_0}{2\pi\sqrt{n_{pro}^2 - n_{L2}^2}} \quad \text{Expression (5)}$$

where $\lambda_0$ represents the average wavelength, in vacuum, of the light propagating through the core layer, $n_{pro}$ represents the refractive index of the material forming the light propagation portion, and $n_{L2}$ represents a refractive index of a material present in a portion sandwiched between the light propagation portion and the substrate.

17. The optical densitometer according to claim 15, wherein a material forming a separation portion between the substrate and the diffraction grating regions has a refractive index smaller than a refractive index of the substrate, and the distance L1 between the diffraction grating region and the substrate satisfies the following Expression (6):

$$\frac{(2m-1)\lambda_0 - 4n_{gr}t_{gr}}{4n_{L1}} - \frac{3\lambda_0}{16n_{L1}} \leq$$

$$L1 \leq \frac{(2m-1)\lambda_0 - 4n_{gr}t_{gr}}{4n_{L1}} + \frac{3\lambda_0}{16n_{L1}} \quad \text{Expression (6)}$$

where $\lambda_0$ represents the average wavelength, in vacuum, of the light propagating through the core layer, $n_{L1}$ represents a refractive index of a material forming the separation portion between the substrate and the diffraction grating region, $t_{gr}$ represents an effective film thickness of the diffraction grating region of the diffraction grating portion, $n_{gr}$ represents a refractive index of a material forming the diffraction grating region of the diffraction grating portion, and m is a natural number.

18. An optical waveguide for use in an optical densitometer for measuring a density of a gas or liquid of interest, the optical waveguide comprising:

a substrate; and a core layer comprising a light propagation portion capable of propagating light in an extending direction of the light propagation portion, and a diffraction grating portion, the diffraction grating portion comprising a diffraction grating region and an extension region connected to the diffraction grating region, and a first optical coupling region included in the extension region and a second optical coupling region included in the light propagation portion being optically coupled with respect to the light propagating through the core layer, wherein at least a portion of the diffraction grating portion is spatially separated from the light propagation portion via a material having a relatively lower refractive index than that of the core layer in a thickness direction, and in a region where the light propagation portion and the diffraction grating portion overlap in plan view, a first distance modification region is provided in which a distance in a thickness direction between the diffraction grating portion and the light propagation portion reduces in a direction approaching from the diffraction grating region toward the first optical coupling region.

* * * * *